US012564403B2

(12) United States Patent (10) Patent No.: US 12,564,403 B2
Banerjee et al. (45) Date of Patent: \*Mar. 3, 2026

(54) LIGATION CLIP LOADING DEVICE

(71) Applicant: Covidien LP, Mansfield, MA (US)

(72) Inventors: Saumya Banerjee, Southington, CT (US); Jacob C. Baril, Norwalk, CT (US); Matthew A. Dinino, Newington, CT (US); Justin J. Thomas, New Haven, CT (US); Eric Brown, Madison, CT (US)

(73) Assignee: Covidien LP, Mansfield, MA (US)

( * ) Notice: Subject to any disclaimer, the term of this patent is extended or adjusted under 35 U.S.C. 154(b) by 207 days.

This patent is subject to a terminal disclaimer.

(21) Appl. No.: 18/482,343

(22) Filed: Oct. 6, 2023

(65) Prior Publication Data

US 2024/0032926 A1 Feb. 1, 2024

Related U.S. Application Data

(63) Continuation of application No. 17/088,225, filed on Nov. 3, 2020, now Pat. No. 11,779,340.

(60) Provisional application No. 62/956,462, filed on Jan. 2, 2020.

(51) Int. Cl.
| | |
|---|---|
| *A61B 17/10* | (2006.01) |
| *A61B 17/00* | (2006.01) |
| *A61B 17/34* | (2006.01) |
| *A61B 34/30* | (2016.01) |

(52) U.S. Cl.
CPC ...... *A61B 17/105* (2013.01); *A61B 17/00234* (2013.01); *A61B 17/3421* (2013.01); *A61B 34/30* (2016.02); *A61B 2034/302* (2016.02)

(58) Field of Classification Search
CPC ............ A61B 17/00234; A61B 17/105; A61B 17/1222; A61B 17/3417; A61B 17/3421; A61B 34/30; A61B 2034/302
USPC ......................................................... 606/142
See application file for complete search history.

(56) References Cited

U.S. PATENT DOCUMENTS

| | | | |
|---|---|---|---|
| 3,120,230 | A | 2/1964 | Skold |
| 3,363,628 | A | 1/1968 | Wood |
| 3,638,847 | A | 2/1972 | Noiles et al. |
| 3,675,688 | A | 7/1972 | Bryan et al. |
| | | (Continued) | |

FOREIGN PATENT DOCUMENTS

| | | |
|---|---|---|
| AU | 2013254887 A1 | 11/2013 |
| CA | 1163889 A | 3/1984 |
| | (Continued) | |

OTHER PUBLICATIONS

Chinese First Office Action corresponding to Patent Application CN 201580073962.2 dated Sep. 5, 2019.

(Continued)

*Primary Examiner* — Jocelin C Tanner
(74) *Attorney, Agent, or Firm* — Draft Masters IP, LLC

(57) ABSTRACT

A ligation clip loading device includes a cannula including a cannula body and an instrument lumen extending through a longitudinal axis of the cannula body, and a stack of ligation clips axially arranged about the instrument lumen. The ligation clips are accessible through a series of slots allowing for loading of an endoscopic clip applier with the ligation clips within a body cavity, such as an intra-abdominal cavity.

20 Claims, 7 Drawing Sheets

(56) References Cited

U.S. PATENT DOCUMENTS

| | | |
|---|---|---|
| 3,735,762 A | 5/1973 | Bryan et al. |
| 3,867,944 A | 2/1975 | Samuels |
| 4,226,242 A | 10/1980 | Jarvik |
| 4,242,902 A | 1/1981 | Green |
| 4,296,751 A | 10/1981 | Blake, III et al. |
| 4,372,316 A | 2/1983 | Blake, III et al. |
| 4,408,603 A | 10/1983 | Blake, III et al. |
| 4,412,539 A | 11/1983 | Jarvik |
| 4,418,694 A | 12/1983 | Beroff et al. |
| 4,471,780 A | 9/1984 | Menges et al. |
| 4,480,640 A | 11/1984 | Becht |
| 4,480,641 A | 11/1984 | Failla et al. |
| 4,487,204 A | 12/1984 | Hrouda |
| 4,487,205 A | 12/1984 | Di Giovanni et al. |
| 4,491,133 A | 1/1985 | Menges et al. |
| 4,492,232 A | 1/1985 | Green |
| 4,498,476 A | 2/1985 | Cerwin et al. |
| 4,500,024 A | 2/1985 | DiGiovanni et al. |
| 4,509,518 A | 4/1985 | McGarry et al. |
| 4,512,345 A | 4/1985 | Green |
| 4,522,207 A | 6/1985 | Klieman et al. |
| 4,532,925 A | 8/1985 | Blake, III |
| 4,534,351 A | 8/1985 | Rothfuss et al. |
| 4,545,377 A | 10/1985 | Cerwin et al. |
| 4,549,544 A | 10/1985 | Favaron |
| 4,556,058 A | 12/1985 | Green |
| 4,557,263 A | 12/1985 | Green |
| 4,562,839 A | 1/1986 | Blake, III et al. |
| 4,572,183 A | 2/1986 | Juska |
| 4,576,165 A | 3/1986 | Green et al. |
| 4,576,166 A | 3/1986 | Montgomery et al. |
| 4,590,937 A | 5/1986 | Deniega |
| 4,598,711 A | 7/1986 | Deniega |
| 4,602,631 A | 7/1986 | Funatsu |
| 4,611,595 A | 9/1986 | Klieman et al. |
| 4,612,932 A | 9/1986 | Caspar et al. |
| 4,616,650 A | 10/1986 | Green et al. |
| 4,616,651 A | 10/1986 | Golden |
| 4,624,254 A | 11/1986 | McGarry et al. |
| 4,637,395 A | 1/1987 | Caspar et al. |
| 4,646,740 A | 3/1987 | Peters et al. |
| 4,647,504 A | 3/1987 | Kimimura et al. |
| 4,658,822 A | 4/1987 | Kees, Jr. |
| 4,660,558 A | 4/1987 | Kees, Jr. |
| 4,662,373 A | 5/1987 | Montgomery et al. |
| 4,662,374 A | 5/1987 | Blake, III |
| 4,671,278 A | 6/1987 | Chin |
| 4,671,282 A | 6/1987 | Tretbar |
| 4,674,504 A | 6/1987 | Klieman et al. |
| 4,681,107 A | 7/1987 | Kees, Jr. |
| 4,696,396 A | 9/1987 | Samuels |
| 4,702,247 A | 10/1987 | Blake, III et al. |
| 4,706,668 A | 11/1987 | Backer |
| 4,712,549 A | 12/1987 | Peters et al. |
| 4,726,372 A | 2/1988 | Perlin |
| 4,733,666 A | 3/1988 | Mercer, Jr. |
| 4,759,364 A | 7/1988 | Boebel |
| 4,765,335 A | 8/1988 | Schmidt et al. |
| 4,777,949 A | 10/1988 | Perlin |
| 4,796,625 A | 1/1989 | Kees, Jr. |
| 4,799,481 A | 1/1989 | Transue et al. |
| 4,815,466 A | 3/1989 | Perlin |
| 4,821,721 A | 4/1989 | Chin et al. |
| 4,822,348 A | 4/1989 | Casey |
| 4,834,096 A | 5/1989 | Oh et al. |
| 4,850,355 A | 7/1989 | Brooks et al. |
| 4,854,317 A | 8/1989 | Braun |
| 4,856,517 A | 8/1989 | Collins et al. |
| 4,929,239 A | 5/1990 | Braun |
| 4,931,058 A | 6/1990 | Cooper |
| 4,934,364 A | 6/1990 | Green |
| 4,957,500 A | 9/1990 | Liang et al. |
| 4,966,603 A | 10/1990 | Focelle et al. |
| 4,967,949 A | 11/1990 | Sandhaus |
| 4,983,176 A | 1/1991 | Cushman et al. |
| 4,988,355 A | 1/1991 | Leveen et al. |
| 5,002,552 A | 3/1991 | Casey |
| 5,026,379 A | 6/1991 | Yoon |
| 5,030,224 A | 7/1991 | Wright et al. |
| 5,030,226 A | 7/1991 | Green et al. |
| 5,032,127 A | 7/1991 | Frazee et al. |
| 5,035,692 A | 7/1991 | Lyon et al. |
| 5,047,038 A | 9/1991 | Peters et al. |
| 5,049,152 A | 9/1991 | Simon et al. |
| 5,049,153 A | 9/1991 | Nakao et al. |
| 5,053,045 A | 10/1991 | Schmidt et al. |
| 5,059,202 A | 10/1991 | Liang et al. |
| 5,062,563 A | 11/1991 | Green et al. |
| 5,062,846 A | 11/1991 | Oh et al. |
| 5,078,731 A | 1/1992 | Hayhurst |
| 5,084,057 A | 1/1992 | Green et al. |
| 5,100,416 A | 3/1992 | Oh et al. |
| 5,100,420 A | 3/1992 | Green et al. |
| 5,104,394 A | 4/1992 | Knoepfler |
| 5,104,395 A | 4/1992 | Thornton et al. |
| 5,112,343 A | 5/1992 | Thornton |
| 5,122,150 A | 6/1992 | Puig |
| 5,127,915 A | 7/1992 | Mattson |
| 5,129,885 A | 7/1992 | Green et al. |
| 5,156,608 A | 10/1992 | Troidl et al. |
| 5,160,339 A | 11/1992 | Chen et al. |
| 5,163,945 A | 11/1992 | Ortiz et al. |
| 5,171,247 A | 12/1992 | Hughett et al. |
| 5,171,249 A | 12/1992 | Stefanchik et al. |
| 5,171,250 A | 12/1992 | Yoon |
| 5,171,251 A | 12/1992 | Bregen et al. |
| 5,171,252 A | 12/1992 | Friedland |
| 5,171,253 A | 12/1992 | Klieman |
| 5,192,288 A | 3/1993 | Thompson et al. |
| 5,197,970 A | 3/1993 | Green et al. |
| 5,199,566 A | 4/1993 | Ortiz et al. |
| 5,201,416 A * | 4/1993 | Taylor ................ A61B 17/1222 |
| | | 206/339 |
| 5,201,746 A | 4/1993 | Shichman |
| 5,201,900 A | 4/1993 | Nardella |
| 5,207,691 A | 5/1993 | Nardella |
| 5,207,692 A | 5/1993 | Kraus et al. |
| 5,217,473 A | 6/1993 | Yoon |
| 5,219,353 A | 6/1993 | Garvey, III et al. |
| 5,246,450 A | 9/1993 | Thornton et al. |
| 5,259,366 A | 11/1993 | Reydel et al. |
| 5,269,792 A | 12/1993 | Kovac et al. |
| 5,281,228 A | 1/1994 | Wolfson |
| 5,282,807 A | 2/1994 | Knoepfler |
| 5,282,808 A | 2/1994 | Kovac et al. |
| 5,282,832 A | 2/1994 | Toso et al. |
| 5,289,963 A | 3/1994 | McGarry et al. |
| 5,290,299 A | 3/1994 | Fain et al. |
| 5,300,081 A | 4/1994 | Young et al. |
| 5,304,183 A | 4/1994 | Gourlay et al. |
| 5,306,280 A | 4/1994 | Bregen et al. |
| 5,306,283 A | 4/1994 | Conners |
| 5,312,426 A | 5/1994 | Segawa et al. |
| 5,330,442 A | 7/1994 | Green et al. |
| 5,330,487 A | 7/1994 | Thornton et al. |
| 5,340,360 A | 8/1994 | Stefanchik |
| 5,342,373 A | 8/1994 | Stefanchik et al. |
| 5,354,304 A | 10/1994 | Allen et al. |
| 5,354,306 A | 10/1994 | Garvey, III et al. |
| 5,356,064 A | 10/1994 | Green et al. |
| 5,359,993 A | 11/1994 | Slater et al. |
| 5,366,458 A | 11/1994 | Korthoff et al. |
| 5,366,459 A | 11/1994 | Yoon |
| 5,368,600 A | 11/1994 | Failla et al. |
| 5,381,943 A | 1/1995 | Allen et al. |
| 5,382,253 A | 1/1995 | Hogendijk |
| 5,382,254 A | 1/1995 | McGarry et al. |
| 5,382,255 A | 1/1995 | Castro et al. |
| 5,383,880 A | 1/1995 | Hooven |
| 5,383,881 A | 1/1995 | Green et al. |
| 5,395,375 A | 3/1995 | Turkel et al. |
| 5,395,381 A | 3/1995 | Green et al. |
| 5,403,327 A | 4/1995 | Thornton et al. |
| 5,409,498 A | 4/1995 | Braddock et al. |

(56)                References Cited

U.S. PATENT DOCUMENTS

| | | | |
|---|---|---|---|
| 5,413,584 A | 5/1995 | Schulze |
| 5,423,835 A | 6/1995 | Green et al. |
| 5,425,740 A | 6/1995 | Hutchinson, Jr. |
| 5,431,667 A | 7/1995 | Thompson et al. |
| 5,431,668 A | 7/1995 | Burbank, III et al. |
| 5,431,669 A | 7/1995 | Thompson et al. |
| 5,439,468 A | 8/1995 | Schulze et al. |
| 5,441,509 A | 8/1995 | Vidal et al. |
| 5,447,513 A | 9/1995 | Davison et al. |
| 5,448,042 A | 9/1995 | Robinson et al. |
| 5,449,365 A | 9/1995 | Green et al. |
| 5,462,555 A | 10/1995 | Bolanos et al. |
| 5,462,558 A | 10/1995 | Kolesa et al. |
| 5,464,416 A | 11/1995 | Steckel |
| 5,474,566 A | 12/1995 | Alesi et al. |
| 5,474,567 A | 12/1995 | Stefanchik et al. |
| 5,474,572 A | 12/1995 | Hayhurst |
| 5,487,499 A | 1/1996 | Sorrentino et al. |
| 5,487,746 A | 1/1996 | Yu et al. |
| 5,501,693 A | 3/1996 | Gravener |
| 5,509,920 A | 4/1996 | Phillips et al. |
| 5,514,149 A | 5/1996 | Green et al. |
| 5,520,701 A | 5/1996 | Lerch |
| 5,527,318 A | 6/1996 | McGarry |
| 5,527,319 A | 6/1996 | Green et al. |
| 5,527,320 A | 6/1996 | Carruthers et al. |
| 5,542,949 A | 8/1996 | Yoon |
| 5,547,474 A | 8/1996 | Kloeckl et al. |
| 5,562,655 A | 10/1996 | Mittelstadt et al. |
| 5,569,274 A | 10/1996 | Rapacki et al. |
| 5,571,121 A | 11/1996 | Heifetz |
| 5,575,802 A | 11/1996 | McQuilkin et al. |
| 5,582,615 A | 12/1996 | Foshee et al. |
| 5,582,616 A | 12/1996 | Bolduc et al. |
| 5,584,840 A | 12/1996 | Ramsey et al. |
| 5,591,178 A | 1/1997 | Green et al. |
| 5,593,414 A | 1/1997 | Shipp et al. |
| 5,593,421 A | 1/1997 | Bauer |
| 5,601,573 A | 2/1997 | Fogelberg et al. |
| 5,601,574 A | 2/1997 | Stefanchik et al. |
| 5,607,436 A | 3/1997 | Pratt et al. |
| 5,618,291 A | 4/1997 | Thompson et al. |
| 5,618,306 A | 4/1997 | Roth et al. |
| 5,620,452 A | 4/1997 | Yoon |
| 5,626,585 A | 5/1997 | Mittelstadt et al. |
| 5,626,586 A | 5/1997 | Pistl et al. |
| 5,626,587 A | 5/1997 | Bishop et al. |
| 5,626,592 A | 5/1997 | Phillips et al. |
| RE35,525 E | 6/1997 | Stefanchik et al. |
| 5,634,930 A | 6/1997 | Thornton et al. |
| 5,643,291 A | 7/1997 | Pier et al. |
| 5,645,551 A | 7/1997 | Green et al. |
| 5,645,553 A | 7/1997 | Kolesa et al. |
| 5,649,937 A | 7/1997 | Bito et al. |
| 5,653,720 A | 8/1997 | Johnson et al. |
| 5,662,662 A | 9/1997 | Bishop et al. |
| 5,662,676 A | 9/1997 | Koninckx |
| 5,662,679 A | 9/1997 | Voss et al. |
| 5,665,097 A | 9/1997 | Baker et al. |
| 5,676,676 A | 10/1997 | Porter |
| 5,681,330 A | 10/1997 | Hughett et al. |
| 5,683,405 A | 11/1997 | Yacoubian et al. |
| 5,695,502 A | 12/1997 | Pier et al. |
| 5,695,505 A | 12/1997 | Yoon |
| 5,697,938 A | 12/1997 | Jensen et al. |
| 5,697,942 A | 12/1997 | Palti |
| 5,700,270 A | 12/1997 | Peyser et al. |
| 5,700,271 A | 12/1997 | Whitfield et al. |
| 5,702,048 A | 12/1997 | Eberlin |
| 5,709,706 A | 1/1998 | Kienzle et al. |
| 5,713,911 A | 2/1998 | Racenet et al. |
| 5,713,912 A | 2/1998 | Porter |
| 5,720,756 A | 2/1998 | Green et al. |
| 5,722,982 A | 3/1998 | Ferreira et al. |
| 5,725,537 A | 3/1998 | Green et al. |
| 5,725,538 A | 3/1998 | Green et al. |
| 5,725,542 A | 3/1998 | Yoon |
| 5,733,295 A | 3/1998 | Back et al. |
| 5,743,310 A | 4/1998 | Moran |
| 5,749,881 A | 5/1998 | Sackier et al. |
| 5,755,726 A | 5/1998 | Pratt et al. |
| 5,766,189 A | 6/1998 | Matsuno |
| 5,769,857 A | 6/1998 | Reztzov et al. |
| 5,772,673 A | 6/1998 | Cuny et al. |
| 5,776,146 A | 7/1998 | Sackier et al. |
| 5,776,147 A | 7/1998 | Dolendo |
| 5,779,718 A | 7/1998 | Green et al. |
| 5,779,720 A | 7/1998 | Walder-Utz et al. |
| 5,782,844 A | 7/1998 | Yoon et al. |
| 5,788,698 A | 8/1998 | Savornin |
| 5,792,149 A | 8/1998 | Sherts et al. |
| 5,792,150 A | 8/1998 | Pratt et al. |
| 5,797,922 A | 8/1998 | Hessel et al. |
| 5,810,853 A | 9/1998 | Yoon |
| 5,817,116 A | 10/1998 | Takahashi et al. |
| 5,827,306 A | 10/1998 | Yoon |
| 5,827,323 A | 10/1998 | Klieman et al. |
| 5,833,695 A | 11/1998 | Yoon |
| 5,833,696 A | 11/1998 | Whitfield et al. |
| 5,833,700 A | 11/1998 | Fogelberg et al. |
| 5,835,199 A | 11/1998 | Phillips et al. |
| 5,843,097 A | 12/1998 | Mayenberger et al. |
| 5,843,101 A | 12/1998 | Fry |
| 5,846,255 A | 12/1998 | Casey |
| 5,849,019 A | 12/1998 | Yoon |
| 5,858,018 A | 1/1999 | Shipp et al. |
| 5,861,005 A | 1/1999 | Kontos |
| 5,868,759 A | 2/1999 | Peyser et al. |
| 5,868,761 A | 2/1999 | Nicholas et al. |
| 5,876,410 A | 3/1999 | Petillo |
| 5,895,394 A | 4/1999 | Kienzle et al. |
| 5,897,565 A | 4/1999 | Foster |
| 5,904,693 A | 5/1999 | Dicesare et al. |
| 5,906,625 A | 5/1999 | Bito et al. |
| 5,913,862 A | 6/1999 | Ramsey et al. |
| 5,913,876 A | 6/1999 | Taylor et al. |
| 5,918,791 A | 7/1999 | Sorrentino et al. |
| 5,921,991 A | 7/1999 | Whitehead et al. |
| 5,921,996 A | 7/1999 | Sherman |
| 5,921,997 A | 7/1999 | Fogelberg et al. |
| 5,928,251 A | 7/1999 | Aranyi et al. |
| 5,938,667 A | 8/1999 | Peyser et al. |
| 5,951,574 A | 9/1999 | Stefanchik et al. |
| 5,972,003 A | 10/1999 | Rousseau et al. |
| 5,976,159 A | 11/1999 | Bolduc et al. |
| 5,993,465 A | 11/1999 | Shipp et al. |
| 6,004,335 A | 12/1999 | Vaitekunas et al. |
| 6,009,551 A | 12/1999 | Sheynblat |
| 6,017,358 A | 1/2000 | Yoon et al. |
| 6,044,971 A | 4/2000 | Esposito et al. |
| 6,045,560 A | 4/2000 | McKean et al. |
| 6,053,908 A | 4/2000 | Crainich et al. |
| RE36,720 E | 5/2000 | Green et al. |
| 6,059,799 A | 5/2000 | Aranyi et al. |
| 6,099,536 A | 8/2000 | Petillo |
| 6,099,537 A | 8/2000 | Sugai et al. |
| 6,139,555 A | 10/2000 | Hart et al. |
| 6,210,418 B1 | 4/2001 | Storz et al. |
| 6,217,590 B1 | 4/2001 | Levinson |
| 6,228,097 B1 | 5/2001 | Levinson et al. |
| 6,241,740 B1 | 6/2001 | Davis et al. |
| 6,258,105 B1 | 7/2001 | Hart et al. |
| 6,261,302 B1 | 7/2001 | Voegele et al. |
| 6,273,898 B1 | 8/2001 | Kienzle et al. |
| 6,277,131 B1 | 8/2001 | Kalikow |
| 6,306,149 B1 | 10/2001 | Meade |
| 6,318,619 B1 | 11/2001 | Lee |
| 6,322,571 B1 | 11/2001 | Adams |
| 6,350,269 B1 | 2/2002 | Shipp et al. |
| 6,352,541 B1 | 3/2002 | Kienzle et al. |
| 6,391,035 B1 | 5/2002 | Appleby et al. |
| 6,419,682 B1 * | 7/2002 | Appleby ............ A61B 17/1222 |
| | | 206/339 |
| 6,423,079 B1 | 7/2002 | Blake, III |

(56) References Cited

U.S. PATENT DOCUMENTS

| | | |
|---|---|---|
| 6,428,548 B1 | 8/2002 | Durgin et al. |
| 6,440,144 B1 | 8/2002 | Bacher |
| 6,461,363 B1 | 10/2002 | Gadberry et al. |
| 6,464,710 B1 | 10/2002 | Foster |
| 6,494,886 B1 | 12/2002 | Wilk et al. |
| 6,517,536 B2 | 2/2003 | Hooven et al. |
| 6,520,972 B2 | 2/2003 | Peters |
| 6,527,786 B1 | 3/2003 | Davis et al. |
| 6,537,289 B1 | 3/2003 | Kayan et al. |
| 6,546,935 B2 | 4/2003 | Hooven |
| 6,551,333 B2 | 4/2003 | Kuhns et al. |
| 6,562,051 B1 | 5/2003 | Bolduc et al. |
| 6,569,171 B2 | 5/2003 | DeGuillebon et al. |
| 6,579,304 B1 | 6/2003 | Hart et al. |
| 6,599,298 B1 | 7/2003 | Forster et al. |
| 6,602,252 B2 | 8/2003 | Mollenauer |
| 6,607,540 B1 | 8/2003 | Shipp |
| 6,613,060 B2 | 9/2003 | Adams et al. |
| 6,626,916 B1 | 9/2003 | Yeung et al. |
| 6,626,922 B1 | 9/2003 | Hart et al. |
| 6,648,898 B1 | 11/2003 | Baxter |
| 6,652,538 B2 | 11/2003 | Kayan et al. |
| 6,652,539 B2 | 11/2003 | Shipp et al. |
| 6,656,193 B2 | 12/2003 | Grant et al. |
| 6,673,083 B1 | 1/2004 | Kayan et al. |
| 6,676,659 B2 | 1/2004 | Hutchins et al. |
| 6,679,894 B2 | 1/2004 | Damarati |
| RE38,445 E | 2/2004 | Pistl et al. |
| 6,695,854 B1 | 2/2004 | Kayan et al. |
| 6,706,057 B1 | 3/2004 | Bidoia et al. |
| 6,716,226 B2 | 4/2004 | Sixto, Jr. et al. |
| 6,723,109 B2 | 4/2004 | Solingen |
| 6,733,514 B2 | 5/2004 | Miser |
| 6,743,240 B2 | 6/2004 | Smith et al. |
| 6,743,241 B2 | 6/2004 | Kerr |
| 6,773,438 B1 | 8/2004 | Knodel et al. |
| 6,773,440 B2 | 8/2004 | Gannoe et al. |
| 6,776,783 B1 | 8/2004 | Frantzen et al. |
| 6,776,784 B2 | 8/2004 | Ginn |
| 6,780,195 B2 | 8/2004 | Porat |
| 6,793,663 B2 | 9/2004 | Kneifel et al. |
| 6,793,664 B2 | 9/2004 | Mazzocchi et al. |
| 6,802,848 B2 | 10/2004 | Anderson et al. |
| 6,814,742 B2 | 11/2004 | Kimura et al. |
| 6,818,009 B2 | 11/2004 | Hart et al. |
| 6,821,273 B2 | 11/2004 | Mollenauer |
| 6,821,284 B2 | 11/2004 | Sturtz et al. |
| 6,821,285 B2 | 11/2004 | Laufer et al. |
| 6,824,547 B2 | 11/2004 | Wilson, Jr. et al. |
| 6,824,548 B2 | 11/2004 | Smith et al. |
| 6,835,199 B2 | 12/2004 | McGuckin, Jr. et al. |
| 6,835,200 B2 | 12/2004 | Laufer et al. |
| 6,837,893 B2 | 1/2005 | Miller |
| 6,837,894 B2 | 1/2005 | Pugsley, Jr. et al. |
| 6,837,895 B2 | 1/2005 | Mayenberger |
| 6,840,945 B2 | 1/2005 | Manetakis et al. |
| 6,843,794 B2 | 1/2005 | Sixto, Jr. et al. |
| 6,849,078 B2 | 2/2005 | Durgin et al. |
| 6,849,079 B1 | 2/2005 | Blake, III et al. |
| 6,853,879 B2 | 2/2005 | Sunaoshi |
| 6,869,435 B2 | 3/2005 | Blake, III |
| 6,869,436 B2 | 3/2005 | Wendlandt |
| 6,889,116 B2 | 5/2005 | Jinno |
| 6,896,676 B2 | 5/2005 | Zubok et al. |
| 6,896,682 B1 | 5/2005 | McClellan et al. |
| 6,896,684 B2 | 5/2005 | Monassevitch et al. |
| 6,905,503 B2 | 6/2005 | Gifford, III et al. |
| 6,911,032 B2 | 6/2005 | Jugenheimer et al. |
| 6,911,033 B2 | 6/2005 | de Guillebon et al. |
| 6,913,607 B2 | 7/2005 | Ainsworth et al. |
| 6,916,327 B2 | 7/2005 | Northrup, III et al. |
| 6,916,332 B2 | 7/2005 | Adams |
| 6,923,818 B2 | 8/2005 | Muramatsu et al. |
| 6,939,356 B2 | 9/2005 | Debbas |
| 6,942,674 B2 | 9/2005 | Belef et al. |
| 6,942,676 B2 | 9/2005 | Buelna |
| 6,945,978 B1 | 9/2005 | Hyde |
| 6,945,979 B2 | 9/2005 | Kortenbach et al. |
| 6,949,107 B2 | 9/2005 | McGuckin, Jr. et al. |
| 6,953,465 B2 | 10/2005 | Dieck et al. |
| 6,955,643 B2 | 10/2005 | Gellman et al. |
| 6,959,852 B2 | 11/2005 | Shelton, IV et al. |
| 6,960,218 B2 | 11/2005 | Rennich |
| 6,960,221 B2 | 11/2005 | Ho et al. |
| 6,962,594 B1 | 11/2005 | Thevenet |
| 6,963,792 B1 | 11/2005 | Green |
| 6,964,363 B2 | 11/2005 | Wales et al. |
| 6,964,668 B2 | 11/2005 | Modesitt et al. |
| 6,966,875 B1 | 11/2005 | Longobardi |
| 6,966,917 B1 | 11/2005 | Suyker et al. |
| 6,966,919 B2 | 11/2005 | Sixto, Jr. et al. |
| 6,969,391 B1 | 11/2005 | Gazzani |
| 6,972,023 B2 | 12/2005 | Whayne et al. |
| 6,972,027 B2 | 12/2005 | Fallin et al. |
| 6,973,770 B2 | 12/2005 | Schnipke et al. |
| 6,974,462 B2 | 12/2005 | Sater |
| 6,974,466 B2 | 12/2005 | Ahmed et al. |
| 6,974,475 B1 | 12/2005 | Wall |
| 6,981,505 B2 | 1/2006 | Krause et al. |
| 6,981,628 B2 | 1/2006 | Wales |
| 6,991,635 B2 | 1/2006 | Takamoto et al. |
| 7,001,399 B2 | 2/2006 | Damarati |
| 7,037,315 B2 | 5/2006 | Sancoff et al. |
| 7,041,119 B2 | 5/2006 | Green |
| 7,052,504 B2 | 5/2006 | Hughett |
| 7,056,330 B2 | 6/2006 | Gayton |
| 7,070,602 B2 | 7/2006 | Smith et al. |
| 7,108,700 B2 | 9/2006 | Chan |
| 7,108,703 B2 | 9/2006 | Danitz et al. |
| 7,141,056 B2 | 11/2006 | Manetakis |
| 7,144,402 B2 | 12/2006 | Kuester, III |
| 7,175,648 B2 | 2/2007 | Nakao |
| 7,179,265 B2 | 2/2007 | Manetakis et al. |
| 7,207,997 B2 | 4/2007 | Shipp et al. |
| 7,211,091 B2 | 5/2007 | Fowler et al. |
| 7,211,092 B2 | 5/2007 | Hughett |
| 7,213,736 B2 | 5/2007 | Wales et al. |
| 7,214,230 B2 | 5/2007 | Brock et al. |
| 7,214,232 B2 | 5/2007 | Bowman et al. |
| 7,223,271 B2 | 5/2007 | Muramatsu et al. |
| 7,223,272 B2 | 5/2007 | Francese et al. |
| 7,232,445 B2 | 6/2007 | Kortenbach et al. |
| 7,238,191 B2 | 7/2007 | Bachmann |
| 7,261,724 B2 | 8/2007 | Molitor et al. |
| 7,261,725 B2 | 8/2007 | Binmoeller |
| 7,264,625 B1 | 9/2007 | Buncke |
| 7,288,098 B2 | 10/2007 | Huitema et al. |
| 7,297,149 B2 | 11/2007 | Vitali et al. |
| 7,312,188 B2 | 12/2007 | Kiso |
| 7,316,693 B2 | 1/2008 | Viola |
| 7,316,696 B2 | 1/2008 | Wilson, Jr. et al. |
| 7,322,995 B2 | 1/2008 | Buckman et al. |
| 7,326,223 B2 | 2/2008 | Wilson, Jr. |
| 7,329,266 B2 | 2/2008 | Royse et al. |
| 7,331,968 B2 | 2/2008 | Arp et al. |
| 7,338,503 B2 | 3/2008 | Rosenberg et al. |
| 7,357,805 B2 | 4/2008 | Masuda et al. |
| 7,367,939 B2 | 5/2008 | Smith et al. |
| 7,407,074 B2 | 8/2008 | Ortiz et al. |
| 7,419,495 B2 | 9/2008 | Menn et al. |
| 7,422,137 B2 | 9/2008 | Manzo |
| 7,431,724 B2 | 10/2008 | Manetakis et al. |
| 7,452,327 B2 | 11/2008 | Durgin et al. |
| 7,485,124 B2 | 2/2009 | Kuhns et al. |
| 7,488,335 B2 | 2/2009 | Sgro |
| 7,510,562 B2 | 3/2009 | Lindsay |
| 7,552,853 B2 | 6/2009 | Mas et al. |
| 7,559,937 B2 | 7/2009 | de la Torre et al. |
| 7,572,266 B2 | 8/2009 | Young et al. |
| 7,578,827 B2 | 8/2009 | Gadberry et al. |
| 7,582,095 B2 | 9/2009 | Shipp et al. |
| 7,585,304 B2 | 9/2009 | Hughett |
| 7,615,058 B2 | 11/2009 | Sixto, Jr. et al. |
| 7,615,060 B2 | 11/2009 | Stokes et al. |

(56)                References Cited

U.S. PATENT DOCUMENTS

| | | | |
|---|---|---|---|
| 7,621,926 B2 | 11/2009 | Wixey et al. |
| 7,637,917 B2 | 12/2009 | Whitfield et al. |
| 7,644,848 B2 | 1/2010 | Swayze et al. |
| 7,686,820 B2 | 3/2010 | Huitema et al. |
| 7,695,482 B2 | 4/2010 | Viola |
| 7,717,926 B2 | 5/2010 | Whitfield et al. |
| 7,727,247 B2 | 6/2010 | Kimura et al. |
| 7,727,248 B2 | 6/2010 | Smith et al. |
| 7,731,724 B2 | 6/2010 | Huitema et al. |
| 7,731,725 B2 | 6/2010 | Gadberry et al. |
| 7,736,388 B2 | 6/2010 | Goldfarb et al. |
| 7,740,639 B2 | 6/2010 | Hummel et al. |
| 7,740,641 B2 | 6/2010 | Huitema |
| 7,744,623 B2 | 6/2010 | Anderson |
| 7,752,853 B2 | 7/2010 | Singh et al. |
| 7,753,250 B2 | 7/2010 | Clauson et al. |
| 7,766,207 B2 | 8/2010 | Mather et al. |
| 7,766,925 B2 | 8/2010 | Stokes et al. |
| 7,770,773 B2 | 8/2010 | Whitman et al. |
| 7,776,058 B2 | 8/2010 | Rosenberg et al. |
| 7,780,688 B2 | 8/2010 | Sakakine et al. |
| 7,793,813 B2 | 9/2010 | Bettuchi |
| 7,806,903 B2 | 10/2010 | Shibata et al. |
| 7,819,886 B2 | 10/2010 | Whitfield et al. |
| 7,823,592 B2 | 11/2010 | Bettuchi et al. |
| 7,857,828 B2 | 12/2010 | Jabba et al. |
| 7,871,416 B2 | 1/2011 | Phillips |
| 7,875,029 B1 | 1/2011 | Hausen |
| 7,887,553 B2 | 2/2011 | Lehman et al. |
| 7,887,554 B2 | 2/2011 | Stokes et al. |
| 7,892,244 B2 | 2/2011 | Monassevitch et al. |
| 7,896,895 B2 | 3/2011 | Boudreaux et al. |
| 7,901,420 B2 | 3/2011 | Dunn |
| 7,905,890 B2 | 3/2011 | Whitfield et al. |
| 7,914,544 B2 | 3/2011 | Nguyen et al. |
| 7,914,551 B2 | 3/2011 | Ortiz et al. |
| 7,942,890 B2 | 5/2011 | D'Agostino et al. |
| 7,947,052 B2 | 5/2011 | Baxter, III et al. |
| 7,954,682 B2 | 6/2011 | Giordano et al. |
| 7,963,433 B2 | 6/2011 | Whitman et al. |
| 7,967,831 B2 | 6/2011 | Rosenberg et al. |
| 7,988,027 B2 | 8/2011 | Olson et al. |
| 7,998,155 B2 | 8/2011 | Manzo |
| 8,011,550 B2 | 9/2011 | Aranyi et al. |
| 8,011,555 B2 | 9/2011 | Tarinelli et al. |
| 8,016,178 B2 | 9/2011 | Olson et al. |
| 8,021,375 B2 | 9/2011 | Aldrich et al. |
| 8,021,378 B2 | 9/2011 | Sixto, Jr. et al. |
| 8,038,686 B2 | 10/2011 | Huitema et al. |
| 8,048,088 B2 | 11/2011 | Green et al. |
| 8,056,565 B2 | 11/2011 | Zergiebel |
| 8,062,310 B2 | 11/2011 | Shibata et al. |
| 8,062,311 B2 | 11/2011 | Litscher et al. |
| 8,062,314 B2 | 11/2011 | Sixto, Jr. et al. |
| 8,066,720 B2 | 11/2011 | Knodel et al. |
| 8,066,721 B2 | 11/2011 | Kortenbach et al. |
| 8,066,722 B2 | 11/2011 | Miyagi et al. |
| 8,070,760 B2 | 12/2011 | Fujita |
| 8,074,857 B2 | 12/2011 | Peterson et al. |
| 8,075,571 B2 | 12/2011 | Vitali et al. |
| 8,080,021 B2 | 12/2011 | Griego |
| 8,083,668 B2 | 12/2011 | Durgin et al. |
| 8,088,061 B2 | 1/2012 | Wells et al. |
| 8,091,755 B2 | 1/2012 | Kayan et al. |
| 8,100,926 B1 | 1/2012 | Filshie et al. |
| 8,128,643 B2 | 3/2012 | Aranyi et al. |
| 8,133,240 B2 | 3/2012 | Damarati |
| 8,137,368 B2 | 3/2012 | Kayan et al. |
| 8,142,451 B2 | 3/2012 | Boulnois et al. |
| 8,157,145 B2 | 4/2012 | Shelton, IV et al. |
| 8,157,149 B2 | 4/2012 | Olson et al. |
| 8,157,151 B2 | 4/2012 | Ingmanson et al. |
| 8,172,859 B2 | 5/2012 | Matsuno et al. |
| 8,172,870 B2 | 5/2012 | Shipp |
| 8,177,797 B2 | 5/2012 | Shimoji et al. |
| 8,182,529 B2 | 5/2012 | Gordon et al. |
| 8,187,290 B2 | 5/2012 | Buckman et al. |
| 8,192,449 B2 | 6/2012 | Maier et al. |
| 8,211,119 B2 | 7/2012 | Palmer et al. |
| 8,211,120 B2 | 7/2012 | Itoh |
| 8,211,124 B2 | 7/2012 | Ainsworth et al. |
| 8,216,255 B2 | 7/2012 | Smith et al. |
| 8,216,257 B2 | 7/2012 | Huitema et al. |
| 8,236,012 B2 | 8/2012 | Molitor et al. |
| 8,241,322 B2 | 8/2012 | Whitman et al. |
| 8,246,634 B2 | 8/2012 | Huitema et al. |
| 8,246,635 B2 | 8/2012 | Huitema |
| 8,262,678 B2 | 9/2012 | Matsuoka et al. |
| 8,262,679 B2 | 9/2012 | Nguyen |
| 8,267,944 B2 | 9/2012 | Sorrentino et al. |
| 8,267,945 B2 | 9/2012 | Nguyen et al. |
| 8,267,946 B2 | 9/2012 | Whitfield et al. |
| 8,272,554 B2 | 9/2012 | Whitman et al. |
| 8,282,655 B2 | 10/2012 | Whitfield et al. |
| 8,287,559 B2 | 10/2012 | Barker et al. |
| 8,308,743 B2 | 11/2012 | Matsuno et al. |
| 8,313,497 B2 | 11/2012 | Walberg et al. |
| 8,328,822 B2 | 12/2012 | Huitema et al. |
| 8,336,556 B2 | 12/2012 | Zergiebel |
| 8,348,130 B2 | 1/2013 | Shah et al. |
| 8,357,171 B2 | 1/2013 | Whitfield et al. |
| 8,366,709 B2 | 2/2013 | Schechter et al. |
| 8,366,726 B2 | 2/2013 | Dennis |
| 8,371,491 B2 | 2/2013 | Huitema et al. |
| 8,372,095 B2 | 2/2013 | Viola |
| 8,382,773 B2 | 2/2013 | Whitfield et al. |
| 8,398,655 B2 | 3/2013 | Cheng et al. |
| 8,403,138 B2 | 3/2013 | Weisshaupt et al. |
| 8,403,945 B2 | 3/2013 | Whitfield et al. |
| 8,403,946 B2 | 3/2013 | Whitfield et al. |
| 8,408,442 B2 | 4/2013 | Racenet et al. |
| 8,409,222 B2 | 4/2013 | Whitfield et al. |
| 8,409,223 B2 | 4/2013 | Sorrentino et al. |
| 8,419,752 B2 | 4/2013 | Sorrentino et al. |
| 8,430,892 B2 | 4/2013 | Bindra et al. |
| 8,444,660 B2 | 5/2013 | Adams et al. |
| 8,465,460 B2 | 6/2013 | Yodfat et al. |
| 8,465,502 B2 | 6/2013 | Zergiebel |
| 8,475,473 B2 | 7/2013 | Vandenbroek et al. |
| 8,480,688 B2 | 7/2013 | Boulnois et al. |
| 8,486,091 B2 | 7/2013 | Sorrentino et al. |
| 8,491,608 B2 | 7/2013 | Sorrentino et al. |
| 8,496,673 B2 | 7/2013 | Nguyen et al. |
| 8,506,580 B2 | 8/2013 | Zergiebel et al. |
| 8,512,357 B2 | 8/2013 | Viola |
| 8,518,055 B1 | 8/2013 | Cardinale et al. |
| 8,523,882 B2 | 9/2013 | Huitema et al. |
| 8,529,585 B2 | 9/2013 | Jacobs et al. |
| 8,529,586 B2 | 9/2013 | Rosenberg et al. |
| 8,529,588 B2 | 9/2013 | Ahlberg et al. |
| 8,545,486 B2 | 10/2013 | Malkowski |
| 8,545,519 B2 | 10/2013 | Aguirre et al. |
| 8,556,920 B2 | 10/2013 | Huitema et al. |
| 8,568,430 B2 | 10/2013 | Shipp |
| 8,579,918 B2 | 11/2013 | Whitfield et al. |
| 8,585,716 B2 | 11/2013 | Roskopf et al. |
| 8,585,717 B2 | 11/2013 | Sorrentino et al. |
| 8,603,109 B2 | 12/2013 | Aranyi et al. |
| 8,623,044 B2 | 1/2014 | Timm et al. |
| 8,628,547 B2 | 1/2014 | Weller et al. |
| 8,632,520 B2 | 1/2014 | Otley |
| 8,636,191 B2 | 1/2014 | Meagher |
| 8,652,151 B2 | 2/2014 | Lehman et al. |
| 8,652,152 B2 | 2/2014 | Aranyi et al. |
| 8,663,247 B2 | 3/2014 | Menn et al. |
| 8,685,048 B2 | 4/2014 | Adams et al. |
| 8,690,899 B2 | 4/2014 | Kogiso et al. |
| 8,708,210 B2 | 4/2014 | Zemlok et al. |
| 8,708,213 B2 | 4/2014 | Shelton, IV et al. |
| 8,709,027 B2 | 4/2014 | Adams et al. |
| 8,715,299 B2 | 5/2014 | Menn et al. |
| 8,720,766 B2 | 5/2014 | Hess et al. |
| 8,734,469 B2 | 5/2014 | Pribanic et al. |
| 8,747,423 B2 | 6/2014 | Whitfield et al. |

(56)  References Cited

U.S. PATENT DOCUMENTS

| | | | |
|---|---|---|---|
| 8,753,356 | B2 | 6/2014 | Vitali et al. |
| 8,758,392 | B2 | 6/2014 | Crainich |
| 8,771,169 | B2 | 7/2014 | Whitman et al. |
| 8,795,302 | B2 | 8/2014 | Wild |
| 8,808,310 | B2 | 8/2014 | Jones et al. |
| 8,814,884 | B2 | 8/2014 | Whitfield et al. |
| 8,821,516 | B2 | 9/2014 | Huitema |
| 8,828,023 | B2 | 9/2014 | Neff et al. |
| 8,839,954 | B2 | 9/2014 | Disch |
| 8,845,659 | B2 | 9/2014 | Whitfield et al. |
| 8,894,665 | B2 | 11/2014 | Sorrentino et al. |
| 8,894,666 | B2 | 11/2014 | Schulz et al. |
| 8,900,253 | B2 | 12/2014 | Aranyi et al. |
| 8,915,930 | B2 | 12/2014 | Huitema et al. |
| 8,915,931 | B2 | 12/2014 | Boudreaux et al. |
| 8,939,974 | B2 | 1/2015 | Boudreaux et al. |
| 8,945,151 | B2 | 2/2015 | Salas |
| 8,950,646 | B2 | 2/2015 | Viola |
| 8,968,337 | B2 | 3/2015 | Whitfield et al. |
| 8,968,342 | B2 | 3/2015 | Wingardner, III et al. |
| 8,973,804 | B2 | 3/2015 | Hess et al. |
| 8,986,343 | B2 | 3/2015 | Bourque et al. |
| 8,998,935 | B2 | 4/2015 | Hart |
| 9,011,464 | B2 | 4/2015 | Zammataro |
| 9,011,465 | B2 | 4/2015 | Whitfield et al. |
| 9,028,511 | B2 | 5/2015 | Weller et al. |
| 9,060,779 | B2 | 6/2015 | Martinez |
| 9,084,604 | B2 | 7/2015 | Litscher et al. |
| 9,089,334 | B2 | 7/2015 | Sorrentino et al. |
| 9,113,892 | B2 | 8/2015 | Malkowski et al. |
| 9,113,893 | B2 | 8/2015 | Sorrentino et al. |
| 9,119,629 | B2 | 9/2015 | Cardinale et al. |
| 9,186,136 | B2 | 11/2015 | Malkowski et al. |
| 9,186,153 | B2 | 11/2015 | Zammataro |
| 9,208,429 | B2 | 12/2015 | Thornton et al. |
| 9,220,507 | B1 | 12/2015 | Patel et al. |
| 9,226,825 | B2 | 1/2016 | Starksen et al. |
| 9,232,947 | B2 | 1/2016 | Brenner et al. |
| 9,265,486 | B2 | 2/2016 | Hughett, Sr. et al. |
| 9,271,737 | B2 | 3/2016 | Castro et al. |
| 9,282,972 | B1 | 3/2016 | Patel et al. |
| 9,282,973 | B2 | 3/2016 | Hughett, Sr. et al. |
| 9,358,011 | B2 | 6/2016 | Sorrentino et al. |
| 9,364,216 | B2 | 6/2016 | Rockrohr et al. |
| 9,364,240 | B2 | 6/2016 | Whitfield et al. |
| 9,370,400 | B2 | 6/2016 | Parihar |
| 9,393,024 | B2 | 7/2016 | Whitfield et al. |
| 9,408,610 | B2 | 8/2016 | Hartoumbekis |
| 9,414,844 | B2 | 8/2016 | Zergiebel et al. |
| 9,433,411 | B2 | 9/2016 | Racenet et al. |
| 9,433,422 | B2 | 9/2016 | Crainich et al. |
| 9,439,654 | B2 | 9/2016 | Sorrentino et al. |
| 9,445,810 | B2 | 9/2016 | Cappola |
| 9,445,820 | B2 | 9/2016 | Whiting |
| 9,456,824 | B2 | 10/2016 | Willett et al. |
| 9,468,444 | B2 | 10/2016 | Menn et al. |
| 9,480,477 | B2 | 11/2016 | Aranyi et al. |
| 9,480,480 | B2 | 11/2016 | Santilli et al. |
| 9,486,225 | B2 | 11/2016 | Michler et al. |
| 9,498,227 | B2 | 11/2016 | Zergiebel et al. |
| 9,504,472 | B2 | 11/2016 | Kamler |
| 9,517,064 | B2 | 12/2016 | Sarradon |
| 9,526,501 | B2 | 12/2016 | Malkowski |
| 9,526,565 | B2 | 12/2016 | Strobl |
| 9,532,787 | B2 | 1/2017 | Zammataro |
| 9,545,254 | B2 | 1/2017 | Sorrentino et al. |
| 9,549,741 | B2 | 1/2017 | Zergiebel |
| 9,561,038 | B2 | 2/2017 | Shelton, IV et al. |
| 9,566,066 | B2 | 2/2017 | Kasvikis |
| 9,597,089 | B2 | 3/2017 | Menn |
| 9,642,627 | B2 | 5/2017 | Zammataro |
| 9,681,877 | B2 | 6/2017 | Blake, III et al. |
| 9,687,247 | B2 | 6/2017 | Aranyi et al. |
| 9,700,324 | B2 | 7/2017 | Mazzucco et al. |
| 9,717,504 | B2 | 8/2017 | Huitema |
| 9,717,505 | B2 | 8/2017 | Whitfield et al. |
| 9,724,163 | B2 | 8/2017 | Orban |
| 9,737,310 | B2 | 8/2017 | Whitfield et al. |
| 9,750,500 | B2 | 9/2017 | Malkowski |
| 9,763,668 | B2 | 9/2017 | Whitfield et al. |
| 9,763,669 | B2 | 9/2017 | Griego |
| 9,775,623 | B2 | 10/2017 | Zammataro et al. |
| 9,775,624 | B2 | 10/2017 | Rockrohr et al. |
| 9,782,164 | B2 | 10/2017 | Mumaw et al. |
| 9,782,181 | B2 | 10/2017 | Vitali et al. |
| 9,808,257 | B2 | 11/2017 | Armenteros et al. |
| 9,848,886 | B2 | 12/2017 | Malkowski et al. |
| 9,855,043 | B2 | 1/2018 | Malkowski |
| 9,883,866 | B2 | 2/2018 | Roundy et al. |
| 9,931,124 | B2 | 4/2018 | Gokharu |
| 9,968,361 | B2 | 5/2018 | Aranyi et al. |
| 9,968,362 | B2 | 5/2018 | Malkowski et al. |
| 10,004,502 | B2 | 6/2018 | Malkowski et al. |
| 10,136,939 | B2 | 11/2018 | Minnelli et al. |
| 10,159,484 | B2 | 12/2018 | Sorrentino et al. |
| 10,159,491 | B2 | 12/2018 | Gokharu |
| 10,159,492 | B2 | 12/2018 | Zammataro |
| 10,166,027 | B2 | 1/2019 | Aranyi et al. |
| 10,231,732 | B1 | 3/2019 | Racenet et al. |
| 10,231,735 | B2 | 3/2019 | Sorrentino et al. |
| 10,231,738 | B2 | 3/2019 | Sorrentino et al. |
| 10,258,346 | B2 | 4/2019 | Zergiebel et al. |
| 10,271,854 | B2 | 4/2019 | Whitfield et al. |
| 10,292,712 | B2 | 5/2019 | Shankarsetty |
| 10,349,936 | B2 | 7/2019 | Rockrohr et al. |
| 10,349,950 | B2 | 7/2019 | Aranyi et al. |
| 10,357,250 | B2 | 7/2019 | Zammataro |
| 10,363,045 | B2 | 7/2019 | Whitfield et al. |
| 10,368,876 | B2 | 8/2019 | Bhatnagar et al. |
| 10,390,831 | B2 | 8/2019 | Holsten et al. |
| 10,426,489 | B2 | 10/2019 | Baril |
| 10,470,765 | B2 | 11/2019 | Malkowski |
| 10,485,538 | B2 | 11/2019 | Whitfield et al. |
| 10,492,795 | B2 | 12/2019 | Williams |
| 10,537,329 | B2 | 1/2020 | Malkowski |
| 10,542,999 | B2 | 1/2020 | Zergiebel |
| 10,548,602 | B2 | 2/2020 | Baril et al. |
| 10,568,635 | B2 | 2/2020 | Whitfield et al. |
| 10,582,931 | B2 | 3/2020 | Mujawar |
| 10,603,038 | B2 | 3/2020 | Mujawar et al. |
| 10,610,236 | B2 | 4/2020 | Baril |
| 10,639,032 | B2 | 5/2020 | Baril et al. |
| 10,639,044 | B2 | 5/2020 | Prior |
| 10,653,429 | B2 | 5/2020 | Baril et al. |
| 10,660,639 | B2 | 5/2020 | Hartoumbekis |
| 10,660,651 | B2 | 5/2020 | Baril et al. |
| 10,660,652 | B2 | 5/2020 | Tan et al. |
| 10,660,723 | B2 | 5/2020 | Baril |
| 10,660,725 | B2 | 5/2020 | Baril et al. |
| 10,675,043 | B2 | 6/2020 | P V R |
| 10,675,112 | B2 | 6/2020 | Baril et al. |
| 10,682,135 | B2 | 6/2020 | Sorrentino et al. |
| 10,682,146 | B2 | 6/2020 | Rockrohr et al. |
| 10,702,278 | B2 | 7/2020 | Tokarz et al. |
| 10,702,279 | B2 | 7/2020 | Xu et al. |
| 10,702,280 | B2 | 7/2020 | Cai et al. |
| 10,709,455 | B2 | 7/2020 | Baril et al. |
| 10,722,235 | B2 | 7/2020 | Baril et al. |
| 10,722,236 | B2 | 7/2020 | Zammataro |
| 10,743,851 | B2 | 8/2020 | Swayze et al. |
| 10,743,886 | B2 | 8/2020 | Malkowski et al. |
| 10,743,887 | B2 | 8/2020 | P V R |
| 10,758,234 | B2 | 9/2020 | Malkowski et al. |
| 10,758,244 | B2 | 9/2020 | Williams |
| 10,758,245 | B2 | 9/2020 | Baril et al. |
| 10,765,431 | B2 | 9/2020 | Hu et al. |
| 10,765,435 | B2 | 9/2020 | Gokharu |
| 10,786,262 | B2 | 9/2020 | Baril et al. |
| 10,786,263 | B2 | 9/2020 | Baril et al. |
| 10,786,273 | B2 | 9/2020 | Baril et al. |
| 10,806,463 | B2 | 10/2020 | Hartoumbekis |
| 10,806,464 | B2 | 10/2020 | Raikar et al. |
| 10,828,036 | B2 | 11/2020 | Baril et al. |
| 10,828,044 | B2 | 11/2020 | Gokharu |

(56) References Cited

U.S. PATENT DOCUMENTS

| | | | |
|---|---|---|---|
| 10,835,260 B2 | 11/2020 | Baril et al. | |
| 10,835,341 B2 | 11/2020 | Baril et al. | |
| 10,849,630 B2 | 12/2020 | P V R | |
| 10,863,992 B2 | 12/2020 | Czernik et al. | |
| 10,932,790 B2 | 3/2021 | Baril et al. | |
| 10,932,791 B2 | 3/2021 | P V R | |
| 10,932,793 B2 | 3/2021 | Yi et al. | |
| 10,945,734 B2 | 3/2021 | Baril et al. | |
| 10,959,737 B2 | 3/2021 | P V R | |
| 10,993,721 B2 | 5/2021 | Baril et al. | |
| 11,026,696 B2 | 6/2021 | Zammataro | |
| 11,033,256 B2 | 6/2021 | Zammataro et al. | |
| 11,051,827 B2 | 7/2021 | Baril et al. | |
| 11,051,828 B2 | 7/2021 | Baril et al. | |
| 11,058,432 B2 | 7/2021 | Bhatnagar et al. | |
| 11,071,553 B2 | 7/2021 | Raikar et al. | |
| 11,116,513 B2 | 9/2021 | Dinino et al. | |
| 11,116,514 B2 | 9/2021 | Yue et al. | |
| 11,134,956 B2 | 10/2021 | Shankarsetty | |
| 11,147,566 B2 | 10/2021 | Pilletere et al. | |
| 11,213,298 B2 | 1/2022 | Sorrentino et al. | |
| 11,213,299 B2 | 1/2022 | Whitfield et al. | |
| 11,779,340 B2 * | 10/2023 | Banerjee | A61B 17/3421 |
| | | | 606/142 |
| 2002/0123742 A1 | 9/2002 | Baxter et al. | |
| 2003/0014060 A1 | 1/2003 | Wilson et al. | |
| 2003/0114867 A1 | 6/2003 | Bolduc et al. | |
| 2003/0208231 A1 | 11/2003 | Williamson et al. | |
| 2003/0229360 A1 | 12/2003 | Gayton | |
| 2004/0097970 A1 | 5/2004 | Hughett | |
| 2004/0097971 A1 | 5/2004 | Hughett | |
| 2004/0133215 A1 | 7/2004 | Baxter | |
| 2004/0138681 A1 | 7/2004 | Pier | |
| 2004/0167545 A1 | 8/2004 | Sadler et al. | |
| 2004/0176783 A1 | 9/2004 | Edoga et al. | |
| 2004/0176784 A1 | 9/2004 | Okada | |
| 2004/0193213 A1 | 9/2004 | Aranyi | |
| 2004/0230198 A1 | 11/2004 | Manzi et al. | |
| 2004/0232197 A1 | 11/2004 | Shelton et al. | |
| 2005/0010242 A1 | 1/2005 | Lindsay | |
| 2005/0090837 A1 | 4/2005 | Sixto, Jr. | |
| 2005/0096670 A1 | 5/2005 | Wellman et al. | |
| 2005/0096671 A1 | 5/2005 | Wellman et al. | |
| 2005/0107810 A1 | 5/2005 | Morales et al. | |
| 2005/0107811 A1 | 5/2005 | Starksen et al. | |
| 2005/0107871 A1 | 5/2005 | Realyvasquez et al. | |
| 2005/0125010 A1 | 6/2005 | Smith et al. | |
| 2005/0149068 A1 | 7/2005 | Williams et al. | |
| 2005/0149069 A1 | 7/2005 | Bertolero et al. | |
| 2005/0171560 A1 | 8/2005 | Hughett | |
| 2005/0175703 A1 | 8/2005 | Hunter | |
| 2005/0177176 A1 | 8/2005 | Gerbi et al. | |
| 2005/0216036 A1 | 9/2005 | Nakao | |
| 2005/0216056 A1 | 9/2005 | Valdevit et al. | |
| 2005/0222665 A1 | 10/2005 | Aranyi | |
| 2005/0228416 A1 | 10/2005 | Burbank et al. | |
| 2005/0234478 A1 | 10/2005 | Wixey et al. | |
| 2005/0256529 A1 | 11/2005 | Yawata et al. | |
| 2005/0267495 A1 | 12/2005 | Ginn et al. | |
| 2005/0273122 A1 | 12/2005 | Theroux et al. | |
| 2005/0277956 A1 | 12/2005 | Francese et al. | |
| 2005/0277958 A1 | 12/2005 | Levinson | |
| 2005/0288689 A1 | 12/2005 | Kammerer et al. | |
| 2006/0000867 A1 | 1/2006 | Shelton et al. | |
| 2006/0004388 A1 | 1/2006 | Whayne et al. | |
| 2006/0009789 A1 | 1/2006 | Gambale et al. | |
| 2006/0009790 A1 | 1/2006 | Blake et al. | |
| 2006/0009792 A1 | 1/2006 | Baker et al. | |
| 2006/0020271 A1 | 1/2006 | Stewart et al. | |
| 2006/0079115 A1 | 4/2006 | Aranyi | |
| 2006/0085015 A1 | 4/2006 | Whitfield et al. | |
| 2006/0085021 A1 | 4/2006 | Wenzler | |
| 2006/0100649 A1 | 5/2006 | Hart | |
| 2006/0124485 A1 | 6/2006 | Kennedy | |
| 2006/0163312 A1 | 7/2006 | Viola et al. | |

| | | | |
|---|---|---|---|
| 2006/0173470 A1 | 8/2006 | Oray et al. | |
| 2006/0190013 A1 | 8/2006 | Menn | |
| 2006/0217749 A1 | 9/2006 | Wilson et al. | |
| 2006/0224165 A1 | 10/2006 | Surti et al. | |
| 2006/0224170 A1 | 10/2006 | Duff | |
| 2006/0235439 A1 | 10/2006 | Molitor et al. | |
| 2006/0241655 A1 | 10/2006 | Viola | |
| 2006/0259045 A1 | 11/2006 | Damarati | |
| 2006/0259049 A1 | 11/2006 | Harada et al. | |
| 2007/0021766 A1 | 1/2007 | Belagali et al. | |
| 2007/0038233 A1 | 2/2007 | Martinez et al. | |
| 2007/0049947 A1 | 3/2007 | Menn et al. | |
| 2007/0049949 A1 | 3/2007 | Manetakis | |
| 2007/0049950 A1 | 3/2007 | Theroux et al. | |
| 2007/0049951 A1 | 3/2007 | Menn | |
| 2007/0083218 A1 | 4/2007 | Morris | |
| 2007/0093790 A1 | 4/2007 | Downey et al. | |
| 2007/0112365 A1 | 5/2007 | Hilal et al. | |
| 2007/0118161 A1 | 5/2007 | Kennedy et al. | |
| 2007/0118174 A1 | 5/2007 | Chu | |
| 2007/0173866 A1 | 7/2007 | Sorrentino et al. | |
| 2007/0185504 A1 | 8/2007 | Manetakis et al. | |
| 2007/0191868 A1 | 8/2007 | Theroux et al. | |
| 2007/0203510 A1 | 8/2007 | Bettuchi | |
| 2007/0276417 A1 | 11/2007 | Mendes, Jr. et al. | |
| 2007/0282355 A1 | 12/2007 | Brown et al. | |
| 2007/0288039 A1 | 12/2007 | Aranyi | |
| 2007/0293875 A1 | 12/2007 | Soetikno et al. | |
| 2008/0004636 A1 | 1/2008 | Walberg et al. | |
| 2008/0045981 A1 | 2/2008 | Margolin et al. | |
| 2008/0051808 A1 | 2/2008 | Rivera et al. | |
| 2008/0103510 A1 | 5/2008 | Taylor et al. | |
| 2008/0147092 A1 | 6/2008 | Rogge et al. | |
| 2008/0167665 A1 | 7/2008 | Arp et al. | |
| 2008/0228199 A1 | 9/2008 | Cropper et al. | |
| 2008/0255413 A1 | 10/2008 | Zemlok et al. | |
| 2008/0255589 A1 | 10/2008 | Blakeney et al. | |
| 2008/0306492 A1 | 12/2008 | Shibata et al. | |
| 2008/0306493 A1 | 12/2008 | Shibata et al. | |
| 2008/0312670 A1 | 12/2008 | Lutze et al. | |
| 2009/0088783 A1 | 4/2009 | Kennedy et al. | |
| 2009/0182193 A1 | 7/2009 | Whitman et al. | |
| 2009/0204115 A1 | 8/2009 | Dees, Jr. et al. | |
| 2009/0209946 A1 | 8/2009 | Swayze et al. | |
| 2009/0228023 A1 | 9/2009 | Cui | |
| 2009/0261142 A1 | 10/2009 | Milliman et al. | |
| 2009/0264904 A1 | 10/2009 | Aldrich et al. | |
| 2009/0312775 A1 | 12/2009 | Gilkey et al. | |
| 2009/0326558 A1 | 12/2009 | Cui et al. | |
| 2010/0057102 A1 | 3/2010 | Sorrentino et al. | |
| 2010/0089970 A1 | 4/2010 | Smith et al. | |
| 2010/0274264 A1 | 10/2010 | Schulz et al. | |
| 2010/0318103 A1 | 12/2010 | Cheng et al. | |
| 2010/0331862 A1 | 12/2010 | Monassevitch et al. | |
| 2011/0028994 A1 | 2/2011 | Whitfield et al. | |
| 2011/0054498 A1 | 3/2011 | Monassevitch et al. | |
| 2011/0087220 A1 | 4/2011 | Felder et al. | |
| 2011/0087268 A1 | 4/2011 | Livneh | |
| 2011/0101066 A1 | 5/2011 | Farascioni et al. | |
| 2011/0144662 A1 | 6/2011 | McLawhorn et al. | |
| 2011/0208211 A1 | 8/2011 | Whitfield et al. | |
| 2011/0208212 A1 | 8/2011 | Zergiebel | |
| 2011/0218554 A1 | 9/2011 | Cheng et al. | |
| 2011/0224700 A1 | 9/2011 | Schmidt et al. | |
| 2011/0295290 A1 | 12/2011 | Whitfield | |
| 2011/0313437 A1 | 12/2011 | Yeh | |
| 2012/0022526 A1 | 1/2012 | Aldridge et al. | |
| 2012/0029534 A1 | 2/2012 | Whitfield | |
| 2012/0046671 A1 | 2/2012 | Matsuoka et al. | |
| 2012/0048759 A1 | 3/2012 | Disch et al. | |
| 2012/0053402 A1 | 3/2012 | Conlon et al. | |
| 2012/0226291 A1 | 9/2012 | Malizia et al. | |
| 2012/0234894 A1 | 9/2012 | Kostrzewski | |
| 2012/0253298 A1 | 10/2012 | Henderson et al. | |
| 2012/0265220 A1 | 10/2012 | Menn | |
| 2012/0330326 A1 | 12/2012 | Creston | |
| 2013/0041379 A1 | 2/2013 | Bodor et al. | |
| 2013/0131697 A1 | 5/2013 | Hartoumbekis | |
| 2013/0165951 A1 | 6/2013 | Blake, III | |

(56)                 References Cited

U.S. PATENT DOCUMENTS

| | | |
|---|---|---|
| 2013/0172909 A1 | 7/2013 | Harris |
| 2013/0172910 A1 | 7/2013 | Malkowski |
| 2013/0175320 A1 | 7/2013 | Mandakolathur Vasudevan et al. |
| 2013/0226200 A1 | 8/2013 | Kappel et al. |
| 2013/0253540 A1 | 9/2013 | Castro et al. |
| 2013/0325057 A1 | 12/2013 | Larson et al. |
| 2014/0005678 A1 | 1/2014 | Shelton, IV et al. |
| 2014/0074143 A1 | 3/2014 | Fitzgerald et al. |
| 2014/0131421 A1 | 5/2014 | Viola |
| 2014/0188159 A1 | 7/2014 | Steege |
| 2014/0252065 A1 | 9/2014 | Hessler et al. |
| 2014/0263565 A1 | 9/2014 | Lytle, IV et al. |
| 2014/0276970 A1 | 9/2014 | Messerly et al. |
| 2014/0309677 A1 | 10/2014 | Baldwin |
| 2014/0324074 A1 | 10/2014 | Crainich et al. |
| 2014/0371728 A1 | 12/2014 | Vaughn |
| 2015/0032131 A1 | 1/2015 | Sorrentino et al. |
| 2015/0190133 A1 | 7/2015 | Penna et al. |
| 2015/0196298 A1 | 7/2015 | Menn et al. |
| 2015/0201953 A1 | 7/2015 | Strobl et al. |
| 2015/0265282 A1 | 9/2015 | Miles et al. |
| 2015/0313452 A1 | 11/2015 | Hasser et al. |
| 2015/0314451 A1 | 11/2015 | Nixon |
| 2015/0327879 A1 | 11/2015 | Garrison et al. |
| 2016/0000428 A1 | 1/2016 | Scirica |
| 2016/0004956 A1 | 1/2016 | Reynolds et al. |
| 2016/0030044 A1 | 2/2016 | Zammataro |
| 2016/0113655 A1 | 4/2016 | Holsten |
| 2016/0151071 A1 | 6/2016 | Tokarz et al. |
| 2016/0166255 A1 | 6/2016 | Fischvogt |
| 2016/0192927 A1 | 7/2016 | Kostrzewski |
| 2016/0213377 A1 | 7/2016 | Shankarsetty |
| 2016/0242767 A1 | 8/2016 | Kasvikis |
| 2016/0242789 A1 | 8/2016 | Sorrentino et al. |
| 2016/0249927 A1 | 9/2016 | Beckman et al. |
| 2016/0256157 A1 | 9/2016 | Rockrohr et al. |
| 2016/0256158 A1 | 9/2016 | Whitfield et al. |
| 2016/0296232 A1 | 10/2016 | Campbell |
| 2016/0296236 A1 | 10/2016 | Whitfield et al. |
| 2016/0338695 A1 | 11/2016 | Hartoumbekis |
| 2016/0338699 A1 | 11/2016 | Sorrentino et al. |
| 2017/0027581 A1 | 2/2017 | Zergiebel et al. |
| 2017/0049449 A1 | 2/2017 | Aranyi et al. |
| 2017/0065277 A1 | 3/2017 | Malkowski |
| 2017/0065281 A1 | 3/2017 | Zammataro |
| 2017/0086846 A1 | 3/2017 | Sorrentino et al. |
| 2017/0086850 A1 | 3/2017 | Zergiebel |
| 2017/0128071 A1 | 5/2017 | Holsten et al. |
| 2017/0165015 A1 | 6/2017 | Hess et al. |
| 2017/0172780 A1 | 6/2017 | Murthy Aravalli |
| 2017/0202567 A1 | 7/2017 | Griffiths et al. |
| 2017/0238936 A1 | 8/2017 | Mujawar |
| 2017/0245921 A1 | 8/2017 | Joseph et al. |
| 2017/0252042 A1 | 9/2017 | Kethman et al. |
| 2017/0258472 A1 | 9/2017 | Aranyi et al. |
| 2017/0290587 A1 | 10/2017 | Schober et al. |
| 2017/0325814 A1 | 11/2017 | Malkowski |
| 2017/0340325 A1 | 11/2017 | Baril et al. |
| 2017/0340331 A1 | 11/2017 | Hu et al. |
| 2017/0340332 A1 | 11/2017 | Whitfield et al. |
| 2017/0360449 A1 | 12/2017 | Rockrohr et al. |
| 2018/0008276 A1 | 1/2018 | Bhatnagar et al. |
| 2018/0008277 A1 | 1/2018 | Baril |
| 2018/0021041 A1 | 1/2018 | Zhang et al. |
| 2018/0070952 A1 | 3/2018 | Malkowski et al. |
| 2018/0116671 A1 | 5/2018 | Prior |
| 2018/0116673 A1 | 5/2018 | Baril et al. |
| 2018/0116674 A1 | 5/2018 | Baril |
| 2018/0116675 A1 | 5/2018 | Baril |
| 2018/0116676 A1 | 5/2018 | Williams |
| 2018/0168660 A1 | 6/2018 | Gokharu |
| 2018/0214156 A1 | 8/2018 | Baril et al. |
| 2018/0221028 A1 | 8/2018 | Williams |
| 2018/0228492 A1 | 8/2018 | Aranyi et al. |
| 2018/0228567 A1 | 8/2018 | Baril et al. |
| 2018/0235632 A1 | 8/2018 | Mujawar et al. |
| 2018/0235633 A1 | 8/2018 | Baril et al. |
| 2018/0235637 A1 | 8/2018 | Xu et al. |
| 2018/0242977 A1 | 8/2018 | Tan et al. |
| 2018/0263624 A1 | 9/2018 | Malkowski et al. |
| 2018/0271526 A1 | 9/2018 | Zammataro |
| 2018/0317927 A1 | 11/2018 | Cai et al. |
| 2018/0317928 A1 | 11/2018 | P V R |
| 2018/0325519 A1 | 11/2018 | Baril et al. |
| 2019/0000449 A1 | 1/2019 | Baril et al. |
| 2019/0000482 A1 | 1/2019 | Hu et al. |
| 2019/0000584 A1 | 1/2019 | Baril |
| 2019/0021738 A1 | 1/2019 | Hartoumbekis |
| 2019/0038375 A1 | 2/2019 | Baril et al. |
| 2019/0046202 A1 | 2/2019 | Baril et al. |
| 2019/0046203 A1 | 2/2019 | Baril et al. |
| 2019/0046207 A1 | 2/2019 | Czernik et al. |
| 2019/0046208 A1 | 2/2019 | Baril et al. |
| 2019/0053806 A1 | 2/2019 | Zhang et al. |
| 2019/0053808 A1 | 2/2019 | Baril et al. |
| 2019/0059904 A1 | 2/2019 | Zammataro |
| 2019/0076147 A1 | 3/2019 | Baril et al. |
| 2019/0076148 A1 | 3/2019 | Baril et al. |
| 2019/0076149 A1 | 3/2019 | Baril et al. |
| 2019/0076150 A1 | 3/2019 | Gokharu |
| 2019/0076210 A1 | 3/2019 | Baril et al. |
| 2019/0133583 A1 | 5/2019 | Baril et al. |
| 2019/0133584 A1 | 5/2019 | Baril et al. |
| 2019/0133590 A1 | 5/2019 | Richard |
| 2019/0133593 A1 | 5/2019 | P V R |
| 2019/0133594 A1 | 5/2019 | Dinino et al. |
| 2019/0133595 A1 | 5/2019 | Baril et al. |
| 2019/0150935 A1 | 5/2019 | Raikar et al. |
| 2019/0159782 A1 | 5/2019 | Kamaraj et al. |
| 2019/0175176 A1 | 6/2019 | Zammataro |
| 2019/0175187 A1 | 6/2019 | P V R |
| 2019/0175188 A1 | 6/2019 | P V R |
| 2019/0175189 A1 | 6/2019 | P V R |
| 2019/0192139 A1 | 6/2019 | Rockrohr et al. |
| 2019/0209177 A1 | 7/2019 | Whitfield et al. |
| 2019/0216464 A1 | 7/2019 | Baril et al. |
| 2019/0239893 A1 | 8/2019 | Shankarsetty |
| 2019/0298377 A1 | 10/2019 | Castro |
| 2019/0321048 A1 | 10/2019 | Dinino et al. |
| 2019/0328391 A1 | 10/2019 | Holsten et al. |
| 2019/0328399 A1 | 10/2019 | Baril et al. |
| 2020/0008806 A1 | 1/2020 | Dinino et al. |
| 2020/0046329 A1 | 2/2020 | Baril et al. |
| 2020/0046359 A1 | 2/2020 | Thomas et al. |
| 2020/0046363 A1 | 2/2020 | Baril et al. |
| 2020/0046365 A1 | 2/2020 | Baril et al. |
| 2020/0046443 A1 | 2/2020 | Baril et al. |
| 2020/0060686 A1 | 2/2020 | Williams |
| 2020/0113569 A1 | 4/2020 | Zergiebel |
| 2020/0129183 A1 | 4/2020 | Baril et al. |
| 2020/0146687 A1 | 5/2020 | Whitfield et al. |
| 2020/0170646 A1 | 6/2020 | Mujawar |
| 2020/0229825 A1 | 7/2020 | P V R |
| 2020/0261095 A1 | 8/2020 | Yi et al. |
| 2020/0315629 A1 | 10/2020 | Xu et al. |
| 2021/0059681 A1 | 3/2021 | Zhang et al. |
| 2021/0169482 A1 | 6/2021 | Baril et al. |
| 2021/0204946 A1 | 7/2021 | Banerjee et al. |
| 2021/0298758 A1 | 9/2021 | Thomas et al. |
| 2021/0401438 A1 | 12/2021 | Pilletere et al. |

FOREIGN PATENT DOCUMENTS

| | | |
|---|---|---|
| CN | 101164502 A | 4/2008 |
| CN | 202699217 U | 1/2013 |
| CN | 103251441 A | 8/2013 |
| CN | 104605911 B | 2/2017 |
| DE | 29520789 U1 | 6/1996 |
| DE | 202005001664 U1 | 5/2005 |
| DE | 202007003398 U1 | 6/2007 |
| EP | 0000756 A1 | 2/1979 |
| EP | 0406724 A1 | 1/1991 |
| EP | 0514139 A2 | 11/1992 |
| EP | 0576835 A2 | 1/1994 |

(56) References Cited

FOREIGN PATENT DOCUMENTS

| EP | 0732078 | A2 | 9/1996 |
|----|---------|----|--------|
| EP | 1769757 | A1 | 4/2007 |
| EP | 3132756 | A1 | 2/2017 |
| EP | 3476331 | A1 | 5/2019 |
| GB | 2073022 | A | 10/1981 |
| JP | 06054858 | | 3/1994 |
| JP | 2003033361 | A | 2/2003 |
| JP | 2006154230 | A | 6/2006 |
| JP | 2006277221 | A | 10/2006 |
| JP | 2008017876 | A | 1/2008 |
| JP | 2008200190 | A | 9/2008 |
| JP | 2011186812 | A | 9/2011 |
| JP | 2013166982 | A | 8/2013 |
| WO | 9003763 | A1 | 4/1990 |
| WO | 9624294 | A1 | 8/1996 |
| WO | 0042922 | A1 | 7/2000 |
| WO | 0166001 | A2 | 9/2001 |
| WO | 0167965 | A1 | 9/2001 |
| WO | 2014169132 | A1 | 10/2014 |
| WO | 2016192096 | A1 | 12/2016 |
| WO | 2016192718 | A2 | 12/2016 |
| WO | 2016197350 | A1 | 12/2016 |
| WO | 2016206015 | A1 | 12/2016 |
| WO | 2017019865 | A1 | 2/2017 |
| WO | 2017084000 | A1 | 5/2017 |
| WO | 2017146138 | A1 | 8/2017 |
| WO | 2018035796 | A1 | 3/2018 |

OTHER PUBLICATIONS

Extended European Search Report corresponding to Patent Application EP 19151805.9 dated Sep. 5, 2019.
Japanese Office Action corresponding to Patent Application JP 2018-537512 dated Sep. 9, 2019.
Extended European Search Report corresponding to Patent Application EP 19170951.8 dated Sep. 26, 2019.
Extended European Search Report corresponding to Patent Application EP 15908020.9 dated Oct. 9, 2019.
Japanese Office Action corresponding to Patent Application JP 2018-534822 dated Oct. 17, 2019.
Extended European Search Report corresponding to Patent Application EP 16884297.9 dated Oct. 31, 2019.
Extended European Search Report corresponding to Patent Application EP 16885490.9 dated Nov. 12, 2019.
Extended European Search Report corresponding to Patent Application EP 19191203.9 dated Dec. 9, 2019.
Extended European Search Report corresponding to Patent Application EP 19191226.0 dated Dec. 10, 2019.
Extended European Search Report corresponding to Patent Application EP 19172130.7 dated Dec. 19, 2019.
European Office Action corresponding to Patent Application EP 18 187 690.5 dated Mar. 23, 2020.
Extended European Search Report corresponding to Patent Application EP 16912243.9 dated Mar. 25, 2020.
Chinese First Office Action corresponding to Patent Application CN 201610694951.2 dated Apr. 23, 2020.
Partial Supplementary European Search Report corresponding to Patent Application EP 18899075.8 dated Jul. 1, 2021.
Australian Examination Report No. 1 corresponding to Patent Application AU 2015413639 dated Jul. 23, 2020.
Chinese First Office Action corresponding to Patent Application CN 201680078525.4 dated Jul. 28, 2020.
Japanese Office Action corresponding to Patent Application JP 2016-217970 dated Sep. 28, 2020.
Extended European Search Report corresponding to Patent Application EP 17895153.9 dated Dec. 17, 2020.
Extended European Search Report corresponding to Patent Application EP 20215391.2 dated Apr. 30, 2021.
Extended European Search Report corresponding to Patent Application EP 18873112.9 dated Oct. 18, 2021.

Extended European Search Report corresponding to Patent Application EP 21164196.4 dated Dec. 17, 2021.
Canadian Office Action dated Sep. 6, 2016 corresponding to Patent Application CA 2,728,538.
Japanese Office Action dated Sep. 1, 2014 corresponding to counterpart Patent Application JP 2011-039024.
Chinese First Office Action corresponding to Chinese Appln. No. CN 2014104295806 dated Aug. 31, 2017.
Extended European Search Report corresponding to European Appln. No. EP 17 17 3508.7 dated Sep. 29, 2017.
Chinese Second Office Action corresponding to Chinese Appln. No. CN 201410076318.8 dated Oct. 10, 2017.
Extended European Search Report corresponding to European Appln. No. EP 17 18 0570.8 dated Dec. 6, 2017.
Extended European Search Report corresponding to Patent Application EP 18154617.7 dated Jun. 25, 2018.
Extended European Search Report corresponding to Patent Application EP 18155158.1 dated Jun. 28, 2018.
Extended European Search Report corresponding to Patent Application EP 15877428.1 dated Jul. 2, 2018.
Extended European Search Report corresponding to Patent Application EP 18157789.1 dated Jul. 5, 2018.
Canadian Office Action corresponding to Patent Application CA 2,972,444 dated Aug. 9, 2018.
Extended European Search Report corresponding to Patent Application EP 18156458.4 dated Sep. 3, 2018.
Extended European Search Report corresponding to Patent Application EP 18171682.0 dated Sep. 18, 2018.
Extended European Search Report corresponding to Patent Application EP 15878354.8 dated Sep. 19, 2018.
Extended European Search Report corresponding to Patent Application EP 18183394.8 dated Sep. 28, 2018.
Extended European Search Report corresponding to Patent Application EP 18163041.9 dated Sep. 28, 2018.
Extended European Search Report corresponding to Patent Application EP 18170524.5 dated Oct. 1, 2018.
Japanese Office Action corresponding to Patent Application JP 2017-536546 dated Oct. 15, 2018.
Extended European Search Report corresponding to Patent Application EP 18187640.0 dated Nov. 30, 2018.
Extended European Search Report corresponding to Patent Application EP 18187690.5 dated Nov. 30, 2018.
Chinese First Office Action corresponding to Patent Application CN 201510696298.9 dated Dec. 3, 2018.
Extended European Search Report corresponding to Patent Application EP 18158143.0 dated Dec. 5, 2018.
International Search Report corresponding to Int'l Patent Appln. PCT/US2018/050316 dated Dec. 31, 2018.
International Search Report corresponding to Int'l Patent Appln. PCT/US2018/050336 dated Jan. 7, 2019.
International Search Report corresponding to Int'l Patent Appln. PCT/US2018/050325 dated Jan. 7, 2019.
International Search Report corresponding to Int'l Patent Appln. PCT/US2018/045306 dated Jan. 16, 2019.
International Search Report corresponding to Int'l Patent Appln. PCT/US2018/050349 dated Jan. 21, 2019.
International Search Report corresponding to Int'l Patent Appln. PCT/US2018/045725 dated Jan. 28, 2019.
Extended European Search Report corresponding to European Patent Application EP 18208630.6 dated Feb. 12, 2019.
International Search Report corresponding to Int'l Patent Appln. PCT/US2018/057910 dated Feb. 22, 2019.
International Search Report corresponding to Int'l Patent Appln. PCT/US2018/057922 dated Feb. 22, 2019.
International Search Report corresponding to Int'l Patent Appln. PCT/US2018/058078 dated Feb. 22, 2019.
International Search Report corresponding to Int'l Patent Appln. PCT/US2018/058603 dated Feb. 22, 2019.
International Search Report corresponding to Int'l Patent Appln. PCT/US2018/057221 dated Mar. 11, 2019.
Extended European Search Report corresponding to European Patent Application EP 18212043.6 dated Apr. 24, 2019.

(56) References Cited

OTHER PUBLICATIONS

Extended European Search Report corresponding to European Patent Application EP 18211565.9 dated Apr. 26, 2019.

Extended European Search Report corresponding to European Patent Application EP 18211921.4 dated Apr. 30, 2019.

Chinese First Office Action corresponding to Chinese Patent Application CN 201510868226.8 dated May 29, 2019.

Extended European Search Report corresponding to European Patent Application EP 15905685.2 dated May 29, 2019.

European Office Action corresponding to European Patent Application EP 17157606.9 dated Jul. 2, 2019.

Extended European Search Report corresponding to European Patent Application EP 15908025.8 dated Jul. 2, 2019.

Extended European Search Report corresponding to European Patent Application EP 18212054.3 dated Jul. 3, 2019.

Partial Supplementary European Search Report corresponding to European Patent Application EP 16884297.9 dated Jul. 30, 2019.

Extended European Search Report corresponding to European Application No. EP 07 25 3905.9, completed Jan. 29, 2008; dated Feb. 7, 2008; (7 Pages).

International Search Report corresponding to International Application No. PCT-US08-58185, completed Sep. 4, 2008; dated Sep. 9, 2008; (2 Pages).

International Search Report corresponding to International Application No. PCT-US08-59859, completed Sep. 14, 2008; dated Sep. 18, 2008; (2 Pages).

Extended European Search Report corresponding to European Application No. EP 07 25 3807.7, completed Nov. 7, 2008; dated Nov. 26, 2008; (11 Pages).

Extended European Search Report corresponding to European Application No. EP 09 25 2049.3, completed Dec. 11, 2009; dated Jan. 12, 2010; (3 Pages).

Extended European Search Report corresponding to European Application No. EP 09 25 2050.1, completed Dec. 23, 2009; dated Jan. 21, 2010; (3 Pages).

Extended European Search Report corresponding to European Application No. EP 09 25 2051.9, completed Dec. 21, 2009; dated Jan. 28, 2010; (3 Pages).

Extended European Search Report corresponding to European Application No. EP 09 25 2052.7, completed Nov. 16, 2009; dated Nov. 24, 2009; (3 Pages).

Extended European Search Report corresponding to European Application No. EP 09 25 2053.5, completed Nov. 24, 2009; dated Dec. 1, 2009; (3 Pages).

Extended European Search Report corresponding to European Application No. EP 09 25 2054.3, completed Jan. 7, 2010; dated Jan. 22, 2010; (3 pages).

Extended European Search Report corresponding to European Application No. EP 09 25 2056.8, completed Jan. 8, 2010; dated Feb. 5, 2010; (3 pages).

Extended European Search Report corresponding to European Application No. EP 10 25 0497.4, completed May 4, 2010; dated May 12, 2010; (6 pages).

Extended European Search Report corresponding to European Application No. EP 10 25 2079.8, completed Mar. 8, 2011; dated Mar. 17, 2011; (3 Pages).

European Search Report corresponding to European Application No. EP 05 81 0218.7, completed Apr. 18, 2011; dated May 20, 2011; (3 Pages).

European Search Report corresponding to European Application No. EP 05 80 7612.6, completed May 2, 2011; dated May 20, 2011; (3 pages).

Extended European Search Report corresponding to European Application No. EP 10 25 1737.2, completed May 9, 2011; dated May 20, 2011; (4 Pages).

Extended European Search Report corresponding to European Application No. EP 11 25 0214.1, completed May 25, 2011; dated Jun. 1, 2011; (3 Pages).

Extended European Search Report corresponding to European Application No. EP 11 00 2681.2, completed May 31, 2011; dated Jun. 10, 2011; (3 Pages).

European Search Report corresponding to European Application No. EP 05 80 2686.5, completed Jan. 9, 2012; dated Jan. 18, 2012; (3 Pages).

Extended European Search Report corresponding to European Application No. EP 12 15 1313.9, completed Mar. 20, 2012 and dated Apr. 12, 2012; (5 Pages).

Extended European Search Report corresponding to European Application No. EP 12 16 1291.5, completed Apr. 24, 2012 and dated May 4, 2012; (5 Pages).

Extended European Search Report corresponding to European Application No. EP 12 16 5891.8, completed Jun. 12, 2012 and dated Jun. 20, 2012; (6 Pages).

Extended European Search Report corresponding to European Application No. EP 12 16 2288.0, completed Jun. 4, 2012 and dated Jul. 7, 2012; (6 Pages).

Extended European Search Report corresponding to European Application No. EP 12 16 4955.2, completed Aug. 23, 2012 and dated Sep. 4, 2012; (5 pages).

Extended European Search Report corresponding to European Application No. EP 11 25 0754.6, completed Oct. 22, 2012 and dated Oct. 31, 2012; (6 Pages).

Extended European Search Report corresponding to European Application No. EP 12 18 6401.1, completed Nov. 22, 2012 and dated Nov. 30, 2012; (7 Pages).

Extended European Search Report corresponding to European Application No. EP 12 18 6448.2, completed Nov. 28, 2012 and dated Dec. 10, 2012; (6 Pages).

Extended European Search Report corresponding to European Application No. EP 12 19 1706.6, completed Dec. 19, 2012 and dated Jan. 8, 2013; (6 Pages).

Extended European Search Report corresponding to EP 12 19 8745.7, completed Mar. 19, 2013 and dated Apr. 11, 2013; (8 Pages).

Extended European Search Report corresponding to EP 12 15 2989.5, completed Apr. 9, 2013 and dated Apr. 18, 2013; (9 Pages).

Extended European Search Report corresponding to EP 08 73 2820.9, completed Jul. 2, 2013 and dated Jul. 9, 2013; (10 Pages).

Extended European Search Report corresponding to EP 13 17 2008.8, completed Aug. 14, 2013 and dated Aug. 28, 2013; (8 Pages).

Extended European Search Report corresponding to EP 13 16 6382.5, completed Nov. 19, 2013 and dated Nov. 28, 2013; (8 Pages).

Extended European Search Report corresponding to EP 11 25 0194.5, completed Nov. 25, 2013 and dated Dec. 3, 2013; (8 Pages).

Extended European Search Report corresponding to EP 10 25 1798.4, completed Dec. 12, 2013 and dated Jan. 2, 2014; (9 Pages).

"Salute II Disposable Fixation Device", Technique Guide—Laparoscopic and Open Inguinal and Ventral Hernia Repair; Davol, A Bard Company, 2006; (7 Pages).

Extended European Search Report corresponding to EP 10 25 2112.7, completed Jul. 29, 2014 and dated Aug. 5, 2014; (8 pp).

Extended European Search Report corresponding to EP 14 15 1673.2, completed Apr. 25, 2014 and dated May 8, 2014; (8 pp).

Japanese Office Action corresponding to JP 2011-160130 dated Dec. 1, 2014.

Chinese Office Action corresponding to CN 201210015011.8 dated Jan. 4, 2015.

Japanese Office Action corresponding to JP 2011-160126 dated Jan. 9, 2015.

Japanese Office Action corresponding to JP 2011-184521 dated Jan. 15, 2015.

Extended European Search Report corresponding to 14 18 2236.1 dated Jan. 20, 2015.

Chinese Office Action corresponding to CN 201110201736.1 dated Feb. 9, 2015.

Extended European Search Report corresponding to EP 14 16 1540.1 dated Feb. 27, 2015.

Australian Office Action corresponding to AU 2010226985 dated Mar. 31, 2015.

(56) References Cited

OTHER PUBLICATIONS

Australian Office Action corresponding to AU 2013211526 dated Apr. 6, 2015.
Australian Office Action corresponding to AU 2011211463 dated Apr. 13, 2015.
Australian Office Action corresponding to AU 2013254887 dated Apr. 14, 2015.
Japanese Office Action corresponding to JP 2013-225272 dated May 1, 2015.
Extended European Search Report for U.S. Appl. No. 20/215,391 dated Apr. 30, 2021.
International Search Report and Written Opinion corresponding to International Application No. PCT/US18/050316 dated Dec. 31, 2018.
International Search Report and Written Opinion corresponding to International Application No. PCT/US18/050325 dated Jan. 7, 2019.
International Search Report and Written Opinion corresponding to International Application No. PCT/US2018/057922 dated Feb. 22, 2019.
Chinese First Office Action corresponding to Patent Application CN 201610055870.8 dated Aug. 1, 2019.
Japanese Office Action corresponding to Patent Application JP 2015-203499 dated Aug. 16, 2019.
Chinese Second Office Action corresponding to Patent Application CN 201510696298.9 dated Aug. 21, 2019.
Japanese Office Action corresponding to Patent Application JP 2018-516433 dated Aug. 21, 2019.
Chinese First Office Action corresponding to Patent Application CN 201580072284.8 dated Aug. 29, 2019.
European Office Action corresponding to EP 12 152 989.5 dated May 4, 2015.
Australian Office Action corresponding to AU 2009212759 dated May 7, 2015.
Chinese Office Action corresponding to Int'l Appln No. CN 201210212642.9 dated Jun. 3, 2015.
European Office Action corresponding to Int'l Appln No. EP 04 719 757.9 dated Jun. 12, 2015.
European Office Action corresponding to Int'l Appln No. EP 13 166 382.5 dated Jun. 19, 2015.
Japanese Office Action corresponding to Int'l Application No. JP 2010-226908 dated Jun. 26, 2015.
Extended European Search Report corresponding to Int'l Application No. EP 15 15 5024.1 dated Jul. 17, 2015.
Extended European Search Report corresponding to Int'l Application No. EP 14 19 2026.4 dated Jul. 17, 2015.
Japanese Office Action corresponding to Int'l Application No. JP 2011-160126 dated Aug. 10, 2015.
Extended European Search Report corresponding to Int'l Application No. EP 14 15 0321.9 dated Sep. 23, 2015.
Extended European Search Report corresponding to Int'l Application No. EP 11 25 0675.3 dated Oct. 7, 2015.
Extended European Search Report corresponding to Int'l Application No. EP 11 25 0674.6 dated Oct. 7, 2015.
Extended European Search Report corresponding to Int'l Application No. EP 12 19 3447.5 dated Oct. 19, 2015.
Canadian Office Action corresponding to Int'l Application No. CA 2,675,875 dated Oct. 26, 2015.
Japanese Office Action corresponding to Int'l Application No. JP 2015-005629 dated Oct. 28, 2015.
Japanese Office Action corresponding to Int'l Application No. JP 2014-245081 dated Oct. 28, 2015.
Canadian Office Action corresponding to Int'l Application No. CA 2,675,921 dated Oct. 30, 2015.

Chinese Office Action corresponding to Int'l Application No. CN 201210555570.8 dated Nov. 2, 2015.
Canadian Office Action corresponding to Int'l Application No. CA 2,676,309 dated Nov. 3, 2015.
Canadian Office Action corresponding to Int'l Application No. CA 2,676,211 dated Nov. 24, 2015.
Canadian Office Action corresponding to Int'l Application No. CA 2,676,547 dated Nov. 25, 2015.
Extended European Search Report corresponding to Int'l Application No. EP 15 17 3809.3 dated Nov. 25, 2015.
Chinese Office Action corresponding to Int'l Application No. CN 201210586814.9 dated Dec. 2, 2015.
Extended European Search Report corresponding to Int'l Application No. EP 12 17 2940.4 dated Dec. 14, 2015.
Chinese First Office Action corresponding to Int'l Appln. No. CN 201210586826.1 dated Dec. 30, 2015.
Extended European Search Report corresponding to Int'l Appln. No. EP 15 18 5362.9 dated Feb. 12, 2016.
Extended European Search Report corresponding to Int'l Appln. No. EP 12 19 7813.4 dated Mar. 7, 2016.
Canadian Office Action corresponding to Int'l Appln. No. CA 2,676,465 dated Mar. 8, 2016.
Japanese Office Action corresponding to Int'l Appln. No. JP 2014-245081 dated Mar. 18, 2016.
Japanese Office Action corresponding to Int'l Appln. No. JP 2015-005629 dated Mar. 18, 2016.
Extended European Search Report corresponding to Int'l Appln. No. EP 15 19 3549.1 dated Mar. 22, 2016.
International Search Report and Written Opinion corresponding to Int'l Appln. No. PCT/CN2015/082199 dated Mar. 31, 2016.
Extended European Search Report corresponding to Int'l Appln. No. EP 15 19 7251.0 dated Apr. 8, 2016.
Extended European Search Report corresponding to Int'l Appln. No. EP 16 15 0739.7 dated May 17, 2016.
Canadian Office Action corresponding to Int'l Appln. No. CA 2,716,672 dated May 31, 2016.
Canadian Office Action corresponding to Int'l Appln. No. CA 2,717,448 dated May 31, 2016.
Canadian Office Action corresponding to Int'l Appln. No. CA 2,721,951 dated Jun. 1, 2016.
Partial European Search Report corresponding to Int'l Appln. No. EP 16 15 0287.7 dated Jun. 16, 2016.
Chinese Second Office Action corresponding to Int'l Appln. No. CN 201210555570.8 dated Jun. 20, 2016.
Chinese First Office Action corresponding to Chinese Appln. No. CN 201410076318.8 dated Jan. 23, 2017.
Extended European Search Report corresponding to European Appln. No. EP 16 18 3184.7 dated Jan. 24, 2017.
Japanese Office Action corresponding to Japanese Appln. No. JP 2016-097807 dated Feb. 14, 2017.
European Office Action corresponding to European Appln. No. EP 12 19 3447.5 dated Apr. 4, 2017.
Chinese First Office Action corresponding to Chinese Appln. No. CN 201410008877.5 dated Apr. 6, 2017.
Extended European Search Report corresponding to European Appln. No. EP 17 15 3714.5 dated May 11, 2017.
Extended European Search Report corresponding to European Appln. No. EP 17 15 8519.3 dated May 19, 2017.
Extended European Search Report corresponding to European Appln. No. EP 17 15 7606.9 dated May 22, 2017.
European Office Action corresponding to European Appln. No. EP 11 25 0674.6 dated May 23, 2017.
Canadian Office Action corresponding to Canadian Appln. No. CA 2,743,402 dated May 30, 2017.
European Office Action corresponding to European Appln. No. EP 16 15 9324.9 dated Aug. 7, 2017.

* cited by examiner

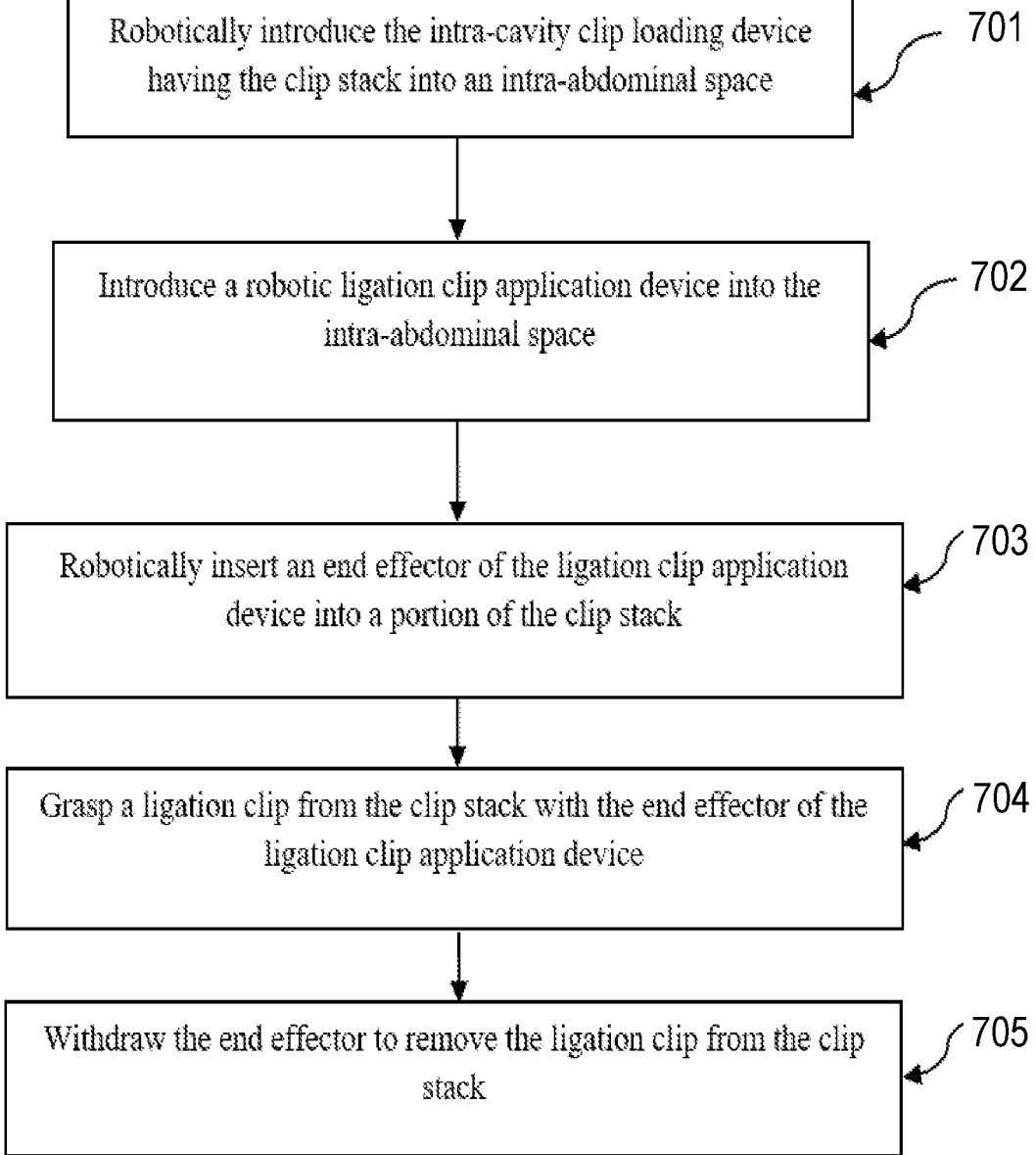

Robotically introduce the intra-cavity clip loading device having the clip stack into an intra-abdominal space — 701

Introduce a robotic ligation clip application device into the intra-abdominal space — 702

Robotically insert an end effector of the ligation clip application device into a portion of the clip stack — 703

Grasp a ligation clip from the clip stack with the end effector of the ligation clip application device — 704

Withdraw the end effector to remove the ligation clip from the clip stack — 705

FIG. 7

LIGATION CLIP LOADING DEVICE

CROSS-REFERENCE TO RELATED APPLICATIONS

This application is a Continuation Application which claims the benefit of and priority to U.S. patent application Ser. No. 17/088,225, filed Nov. 3, 2020, (now U.S. Pat. No. 11,779,340) which claims the benefit of and priority to U.S. Provisional Patent Application Ser. No. 62/956,462, filed Jan. 2, 2020, the entire disclosure of which is incorporated by reference herein.

FIELD

This disclosure is generally related to ligation clips and, more particularly, to a ligation clip loading device for intra-cavity loading of ligation clips to a ligation clip applicator device.

BACKGROUND

Polymeric ligation clips typically include first and second beams that are coupled together at one end by a pivotable connection, e.g., living hinge, such that the first and second beams can be moved in relation to each other between open and clamped positions. The ligation clips can be applied to tissue endoscopically through a small diameter incision or through a small diameter cannula positioned through the incision to minimize trauma to a patient during a surgical procedure.

Typically, when polymeric clips are applied to tissue through a cannula and/or stored within an endoscopic clip applier, the clips are supported in a compressed or partially compressed state to minimize an overall dimension of the clips and facilitate delivery of the clips through the cannula or incision. Storing polymeric clips in a compressed or partially compressed state may impact the condition of the clips which may impact the performance of the clips.

In minimally-invasive surgical procedures, operations are carried out within an internal body cavity through small entrance openings in the body. The entrance openings may be natural passageways of the body or may be surgically created, for example, by making a small incision into which a cannula is inserted.

Minimally-invasive surgical techniques may be used for placement of ligation clips within an internal body cavity, such as an intra-abdominal space, by a ligation clip application device (e.g., endoscopic clip applier). Ligation clips are loaded into an end effector of an endoscopic clip applier and the endoscopic clip applier clamps the ligation clip at a desired site.

SUMMARY

In one aspect of the disclosure, an intra-cavity clip loading device includes a cannula including a cannula body defining an instrument lumen extending along a longitudinal axis of the cannula body. A clip stack is defined in the cannula body. The clip stack includes ligation clips axially arranged about the instrument lumen. Clip retention features are formed in the cannula body. Each clip retention feature holds a ligation clip.

In some aspects of the disclosure, each ligation clip includes a first arm and a second arm defining a central region between the first and second arms. The instrument lumen extends through the central region. The cannula includes an inner wall and an outer wall. The inner wall defines the instrument lumen. The first and second arms of each of the ligation clips are positioned between the inner wall and the outer wall of the cannula. The inner wall of the cannula separates the plurality of ligation clips from the instrument lumen to maintain a fluid integrity of the instrument lumen.

In some aspects of the disclosure, the cannula body includes slots formed in the cannula body. Each slot is associated with a clip retention feature. Each ligation clip is accessible by a clip applier through a respective slot.

In some aspects of the disclosure, the first arm of each ligation clip includes a first boss and the second arm of each ligation clip includes a second boss. The first boss and the second boss are each coupled to a clip retention feature.

In some aspects of the disclosure, the slots are covered by a sheath positioned about the cannula body. The slots may be located proximate a distal end portion of the cannula body.

In some aspects of the disclosure, the cannula includes a mate cap and an instrument seal formed in the mate cap to maintain a predetermined pressure in the instrument lumen.

In some aspects of the disclosure, a distal seal provides a barrier between an internal body cavity and the instrument lumen.

In one aspect of the disclosure, a method of robotic intra-abdominal clip loading includes robotically introducing the intra-cavity clip loading device into an intra-abdominal space. A robotic ligation clip application device is loaded into the intra-abdominal space. The end effector of the ligation clip application device is robotically inserted into a portion of the clip stack. The end effector of the ligation clip application device grasps the ligation clip of the plurality of ligation clips. The end effector of the ligation clip application device is withdrawn to remove the ligation clip from the clip stack defined in the distal end portion of the cannula body.

In some aspects of the disclosure, the end effector of the ligation clip application device is robotically inserted into a slot of the clip stack to grasp the ligation clip. The end effector may be robotically inserted into the slot at a location proximate the distal end portion of the cannula body. The first arm and the second arm of the end effector may be inserted into the portion of the clip stack to grasp the ligation clip. The first arm and the second arm of the ligation clip application device separates the ligation clip from the clip retention feature.

Other features of the disclosure will be appreciated from the following description.

BRIEF DESCRIPTION OF THE DRAWINGS

The accompanying drawings, which are incorporated in and constitute a part of this specification, illustrate aspects and features of the disclosure and, together with the detailed description below, serve to further explain the disclosure, in which:

FIG. 7 is a flow chart of a method of robotic intra-abdominal clip loading in accordance with the disclosure.

DETAILED DESCRIPTION

Figure 1A:
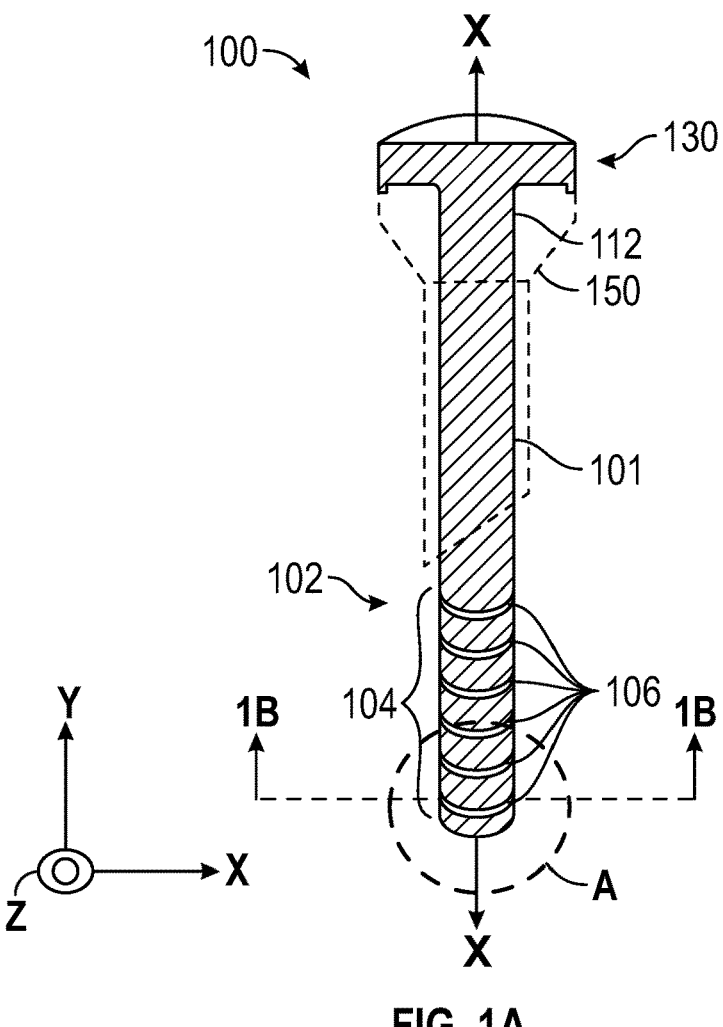
FIG. 1A is a side view of an intra-cavity clip storing and/or loading device in accordance with the disclosure.
Figure 1B:
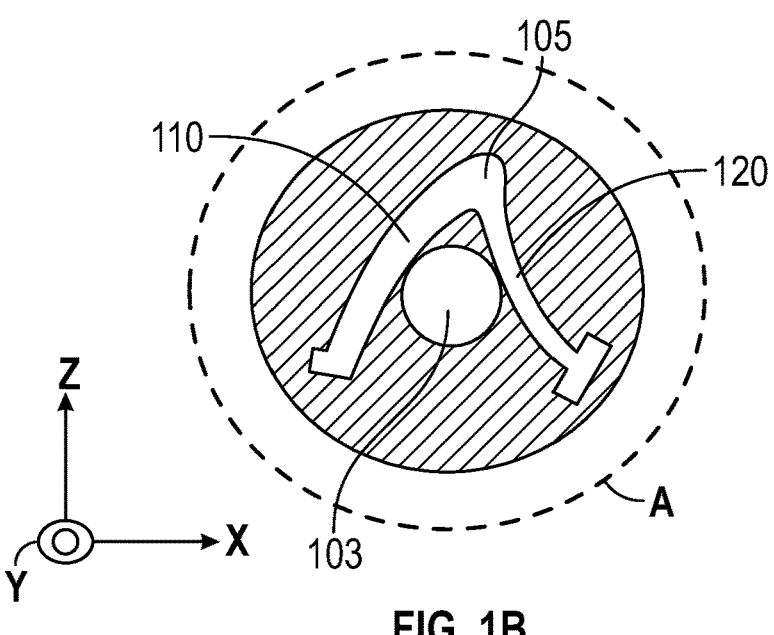
FIG. 1B is a cross-sectional view along line 1B-1B of FIG. 1A.

As used herein, the term "distal" refers to the portion that is being described which is further from a user, while the term "proximal" refers to the portion that is being described which is closer to a user. Further, to the extent consistent, any of the aspects and features detailed herein may be used in conjunction with any or all of the other aspects and features detailed herein.

As used herein, the terms parallel and perpendicular are understood to include relative configurations that are substantially parallel and substantially perpendicular up to about + or − 10 degrees from true parallel and true perpendicular.

Exemplary axes or directions such as an X-axis direction, a Y-axis direction and a Z-axis direction may be illustrated in the accompanying drawings and/or described herein. As an example, the X-axis direction may be perpendicular to the Y-axis direction, and the Z-axis direction may be orthogonal to the X-axis direction and the Y-axis direction.

"About" or "approximately" or "substantially" as used herein may be inclusive of the stated value and means within an acceptable range of variation for the particular value as determined by one of ordinary skill in the art, considering the measurement in question and the error associated with measurement of the particular quantity (e.g., the limitations of the measurement system). For example, "about" may mean within one or more standard variations, or within ±30%, 20%, 10%, 5% of the stated value.

Descriptions of technical features or aspects of an exemplary embodiment of the disclosure should typically be considered as available and applicable to other similar features or aspects in another exemplary embodiment of the disclosure. Accordingly, technical features described herein according to one exemplary embodiment of the disclosure may be applicable to other exemplary embodiments of the disclosure, and thus duplicative descriptions may be omitted herein.

Exemplary embodiments of the disclosure will be described more fully below (e.g., with reference to the accompanying drawings) Like reference numerals may refer to like elements throughout the specification and drawings.

The intra-cavity clip loading devices described herein allow intra-cavity loading of ligation clips while still optionally providing an instrument lumen (e.g., for use by 5 mm instruments). Thus, a single endoscopic port can be employed for intra-cavity ligation clip storing and loading of a ligation clip application device and for providing access to a surgical instrument through the instrument lumen extending between the ligation clips.

FIGS. 1A, 1B, 2A and 2B illustrate an embodiment of an intra-cavity clip loading device 100. The intra-cavity clip loading device 100 includes cannula 101 including distal cannula portion 102 defining an instrument lumen 103 extending along a longitudinal axis "X-X" defined by the cannula 101.

A clip stack 104 is defined in the cannula 101. The clip stack 104 includes ligation clips 105 axially arranged about the instrument lumen 103. The clip stack 104 includes a stack of ligation clips 105 spaced apart from each other such that each ligation clip 105 can be individually removed by a ligation clip application device 201 (see, e.g., FIGS. 2A and 2B). The ligation clip application device 201 may be a robotically controlled device (see, e.g., FIG. 8).

The ligation clips 105 each include a first arm 110 and a second arm 120 positioned at opposite sides of the instrument lumen 103. The instrument lumen 103 allows passage of a surgical instrument through the instrument lumen 103 between the first arm 110 and the second arm 120 of each of the ligation clips 105.

In some aspects of the disclosure, the instrument lumen 103 of cannula 101 may be omitted, and the intra-cavity clip loading device 100 may provide intra-cavity ligation clip loading without providing an access port for an additional surgical instrument. Thus, the clip stack 104 may be defined in the body of an obturator without the presence of the instrument lumen 103.

Figure 2A:
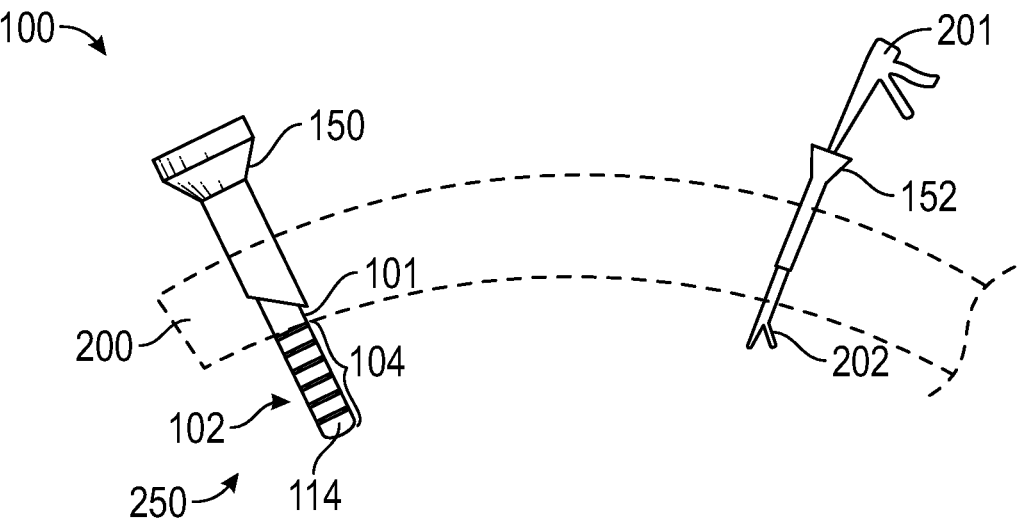
FIG. 2A illustrates the intra-cavity clip loading device of FIG. 1A positioned in a body cavity adjacent to a ligation clip application device.
Figure 2B:
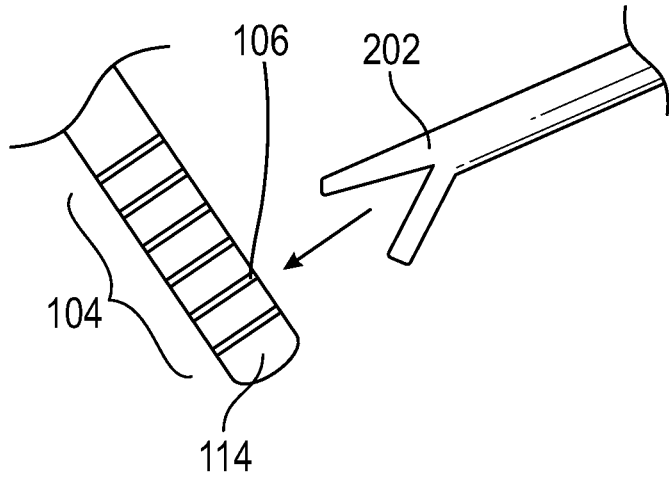
FIG. 2B illustrates loading of a ligation clip from the intra-cavity clip loading device of FIG. 1A to the ligation clip application device.
Figure 3:
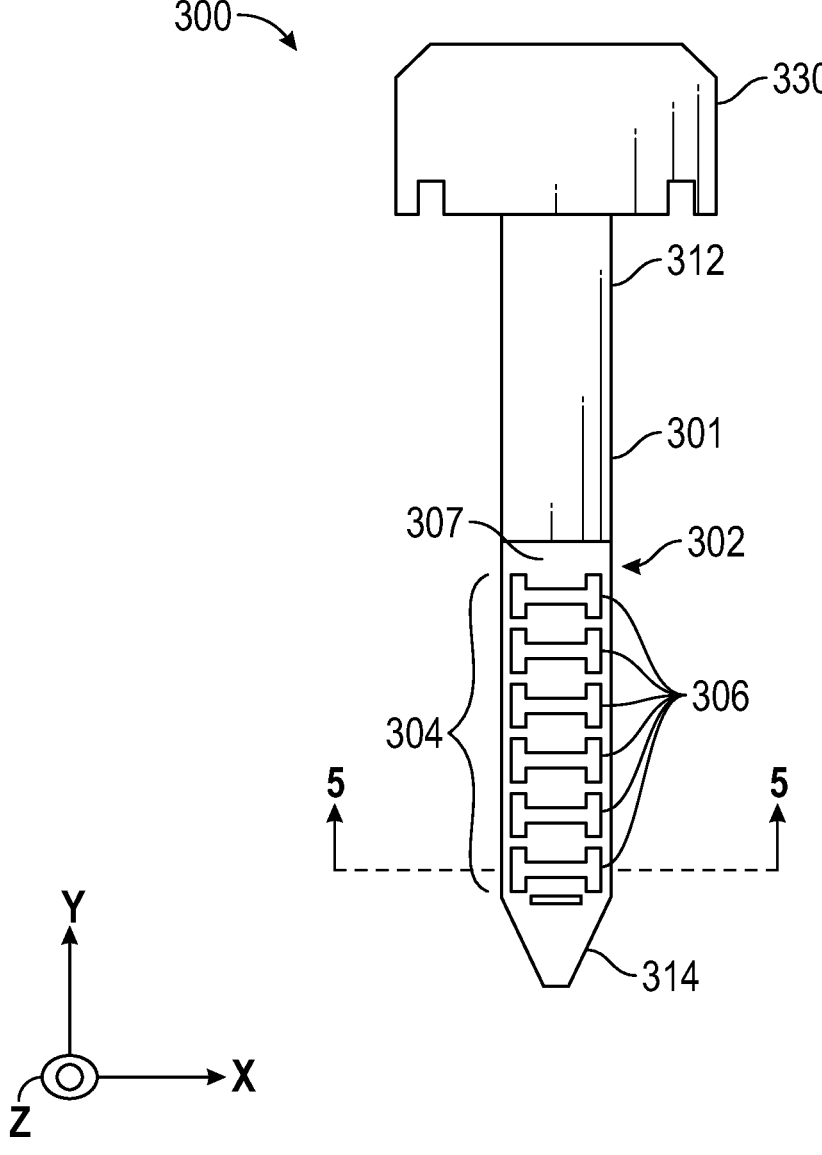
FIG. 3 is a side view of an intra-cavity clip loading device in accordance with another embodiment of the disclosure.
Figure 4:
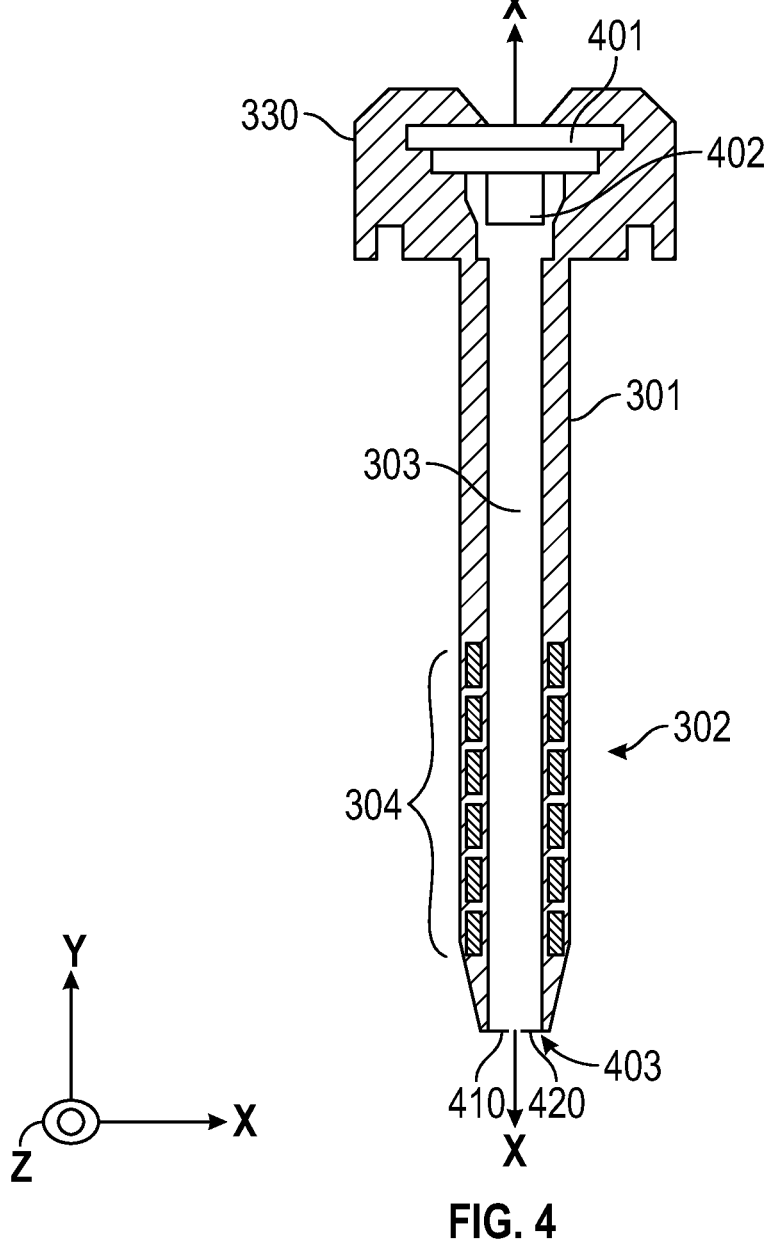
FIG. 4 is an internal cross-sectional view of the intra-cavity clip loading device of FIG. 3.

In use, with specific reference to FIGS. 2A and 2B, the intra-cavity clip loading device 100 may be inserted and secured to an endoscopic port 150 (e.g., by mate cap 130) at a proximal end portion 112 of the cannula 101. The cannula 101 extends through a body cavity wall 200 (e.g., an intra-abdominal wall). A distal end portion 114 of the intra-cavity clip loading device 100 is positioned in an intra-cavity space 250 (e.g., intra-abdominal) such that the ligation clips 105 can be removed by the ligation clip application device 201 without removing the intra-cavity clip loading device 100 from the intra-cavity space. The ligation clip application device 201 may extend through a separate endoscopic port 152. The ligation clip application device 201 may include an end effector 202 (e.g., jaws) configured to grasp and apply ligation clips 105. The end effector 202 is configured for insertion into slots 106 of the clip stack 104 to individually remove ligation clips 105 stored within the intra-cavity space 250.

FIGS. 3-6 illustrate an exemplary intra-cavity clip loading device 300. The intra cavity clip loading device 300 includes a cannula 301 including a cannula body 302 defining an instrument lumen 303 extending along a longitudinal axis "X-X" defined by the cannula body 302. A clip stack 304 is defined in the cannula body 302 (e.g., at a location proximate a distal end thereof). The clip stack 304 includes ligation clips 305 axially arranged about the instrument lumen 303. Clip retention features 501 are formed in the cannula body 302. Each clip retention feature 501 holds a ligation clip 305.

The intra-cavity clip loading device 300 may include a mate cap 330 for securing the intra-cavity clip loading device 300 to an endoscopic port. The mate cap 330 may include an instrument seal 401 and/or a zero seal 402 for allowing access to a surgical instrument through the instrument lumen 303. The instrument seal 401 or the zero seal 402 can maintain a fluid integrity of the instrument lumen 303. A distal seal 403 may be formed at a distal end portion 314 of the cannula body 302. The distal seal 403 may include a first flap 410 and a second flap 420 for allowing passage of a surgical instrument therethrough, while also maintaining a fluid integrity of the instrument lumen 303. The distal seal 403 provides a barrier between an internal body cavity and the instrument lumen 303. It is envisioned that instrument seal 401 and zero seal 402 may be incorporated directly into clip loading device 300.

As an example, the cannula body 302 may have a diameter of from about 12 mm to about 15 mm, and the instrument lumen 303 may have a diameter of from about 3 mm to about 5 mm.

Each ligation clip 305 includes a first arm 310 and a second arm 320 defining a central region between the first and second arms 310 and 320. The first and second arms 310 and 320 may reversibly pivot or flex with respect to each other through compression or flexure of a hinge 331. The instrument lumen 303 extends through the central region between the first and second arms 310 and 320 of each ligation clip 305.

Figure 5:
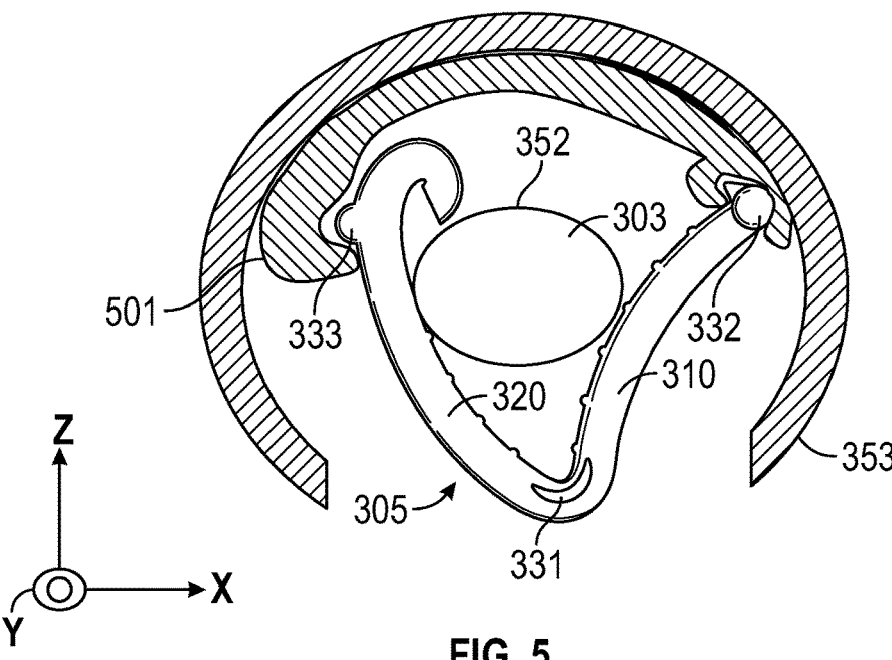
FIG. 5 is a cross-sectional view along line 5-5 of FIG. 3.
Figure 6:
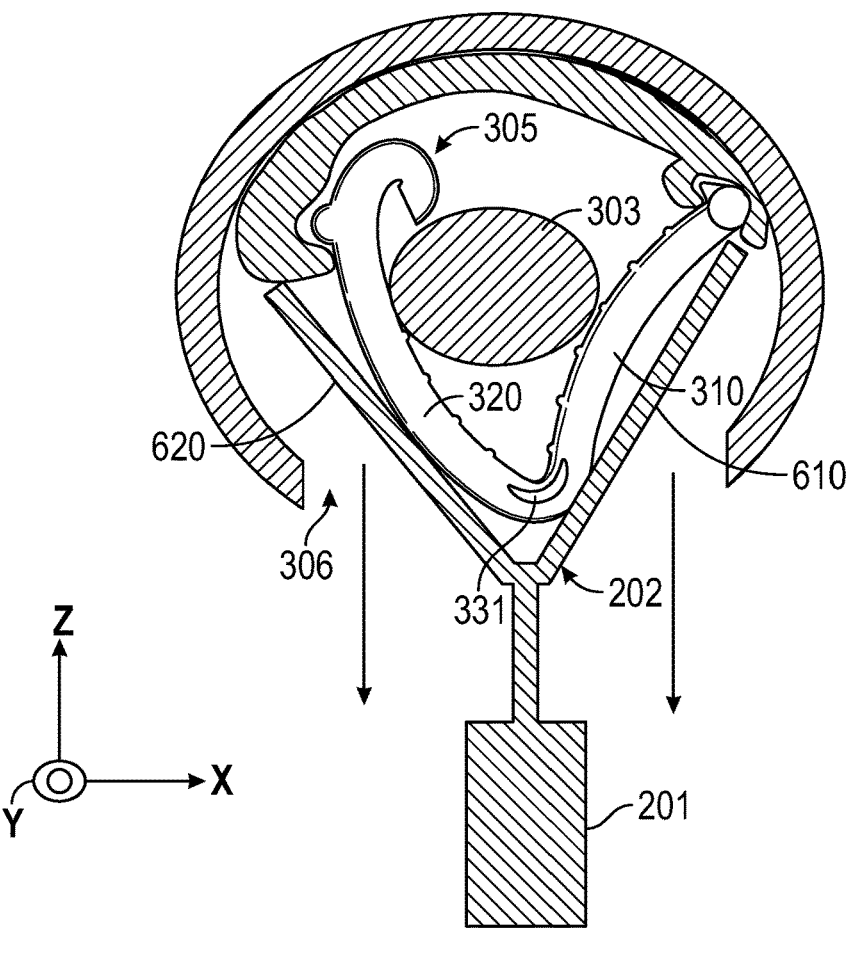
FIG. 6 illustrates loading of a ligation clip from the intra-cavity clip loading device of FIG. 3 to a ligation clip application device.

With reference to FIGS. 5 and 6, the cannula 301 and cannula body 302 include an inner wall 352 and an outer wall 353. The inner wall 352 defines the instrument lumen 303. The first and second arms 310 and 320 of each of the ligation clips 305 are positioned between the inner wall 352 and the outer wall 353 of the cannula 301. The inner wall 352 of the cannula 301 separates the plurality of ligation clips 305 from the instrument lumen 303 to maintain a fluid integrity of the instrument lumen 303.

The cannula body 302 includes slots 306 formed in an outer surface thereof (e.g., outer wall 353). Each slot 306 is associated with a clip retention feature 501. Each ligation clip 305 is accessible by a clip applier (e.g., a ligation clip application device) through a respective slot 306. The use of separate slots 306 each employing a separate clip retention feature 501 allows each ligation clip 305 to be individually securely removed by the clip applier.

The first arm 310 of each ligation clip 305 includes a first boss 332 and the second arm 320 of each ligation clip 305 includes a second boss 333. The first boss 332 and the second boss 333 are each coupled to a clip retention feature 501. Thus, the first and second bosses 332 and 333 may be employed for securing the ligation clips 305 to corresponding clip retention features 501 in corresponding slots 306.

The slots 306 may be covered by a sheath 307 positioned about the cannula body 302. As an example, the sheath 307 may include or may be formed of plastic. The sheath 307 may assist in guiding an end effector 202 of a ligation clip application device 201 into a desired slot 306, and may assist in maintaining ligation clips 305 within slots 306.

The slots 306 may each be located proximate a distal end portion 314 of the cannula body 302. As an example, the clip stack 304 may include a stack of six ligation clips 305 and a six corresponding slots 306.

The cannula 101 and cannula body 102, or the cannula 301 and cannula body 302 may be configured for bladeless insertion by employing a distal tip having bladeless insertion geometry (see, e.g., FIG. 3), in the manner of an obturator or the like.

FIG. 6 illustrates removal of a single ligation clip 305 through a single slot 306 by a ligation clip application device 201. The ligation clip application device 201 may include an end effector 202 having a first arm 210 and a second arm 220. The first arm 210 may grasp a first arm 310 of the ligation clip 305 and the second arm 220 may grasp a second arm 320 of the ligation clip 305. The bosses 332 and/or 333 may be employed by the end effector 202 for grasping the ligation clip 305. The hinge 331 of the ligation clip 305 allows flexing of the first and second arms 310 and 320 toward or away from each other to detach the ligation clip 305 from the clip retention feature 501. Thus, the ligation clip 305 may be freed from the clip retention feature 501 and retracted out of slot 306 while being securely grasped by end effector 202 of ligation clip application device 201.

FIG. 7 is a flowchart illustrating a method of robotic intra-abdominal clip loading. The method includes robotically introducing the intra-cavity clip loading device 100 having the clip stack 104 into an intra-abdominal space (step 701; see, e.g., FIGS. 2A and 2B—intra-cavity space 250). The method includes introducing a robotic ligation clip application device 201 into the intra-abdominal space (step 702). The end effector 202 of the ligation clip application device 201 is robotically inserted into a portion (e.g., a slot 106) of the clip stack 104 (step 703). The end effector 202 of the ligation clip application device 201 grasps the ligation clip 105 (step 704). The end effector 202 of the ligation clip application device 2012 is withdrawn to remove the ligation clip 105 from the clip stack 104 (step 705; see, e.g., FIG. 6).

The end effector 202 of the ligation clip application device 201 is robotically inserted into the slot 106 of the clip stack 104 to grasp the ligation clip 105. The end effector 202 may be robotically inserted into the slot 106 (e.g., at a location proximate the distal end portion 114 of the cannula body 302). The first arm 210 and the second arm 220 of the end effector 202 may be inserted into the portion (e.g., the slot 106) of the clip stack 104 to grasp the ligation clip 105. The first arm 210 and the second arm 220 of the ligation clip application device 201 separates the ligation clip 105 from the clip retention feature 501.

The various embodiments disclosed herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely controls the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

Figure 8:
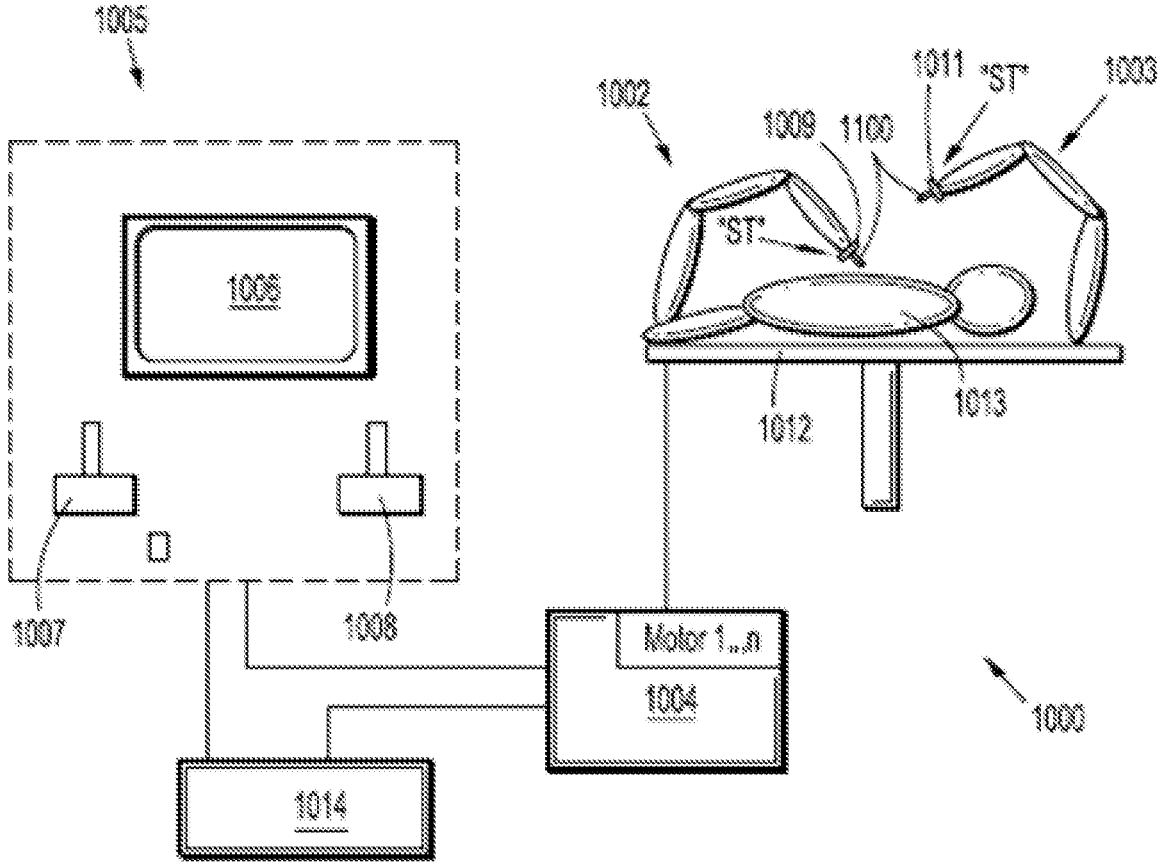
FIG. 8 is a schematic illustration of a robotic surgical system configured for use in accordance with the disclosure.

FIG. 8 illustrates a medical work station shown generally as work station 1000 and generally may include a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a person (not shown), for example a surgeon, may be able to telemanipulate robot arms 1002, 1003 in a first operating mode.

Each of the robot arms 1002, 1003 may include a plurality of members, which are connected through joints, and an attaching device 1009, 1011, to which may be attached, for example, a surgical tool "ST" supporting an end effector 1100, in accordance with any one of several embodiments disclosed herein, as will be described in greater detail below.

Robot arms 1002, 1003 may be driven by electric drives (not shown) that are connected to control device 1004. Control device 1004 (e.g., a computer) may be set up to activate the drives, in particular by means of a computer program, in such a way that robot arms 1002, 1003, their attaching devices 1009, 1011 and thus the surgical tool (including end effector 1100) execute a desired movement according to a movement defined by means of manual input devices 1007, 1008. Control device 1004 may also be set up in such a way that it regulates the movement of robot arms 1002, 1003 and/or of the drives.

Medical work station 1000 may be configured for use on a patient 1013 lying on a patient table 1012 to be treated in a minimally invasive manner by means of end effector 1100. Medical work station 1000 may also include more than two robot arms 1002, 1003, the additional robot arms likewise being connected to control device 1004 and being telemanipulatable by means of operating console 1005. A medical instrument or surgical tool (including an end effector 1100) may also be attached to the additional robot arm. Medical work station 1000 may include a database 1014, in particular coupled to with control device 1004, in which are stored, for example, pre-operative data from patient/living being 1013 and/or anatomical atlases.

From the foregoing and with reference to the various figure drawings, those skilled in the art will appreciate that certain modifications can also be made to the disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An intra-cavity clip loading device, comprising:
a cannula including a cannula body defining an instrument lumen extending along a longitudinal axis of the cannula body, wherein the cannula includes an inner wall and an outer wall, the inner wall defining the instrument lumen;
at least one ligation clip axially arranged about the instrument lumen, wherein the at least one ligation clip includes a first arm and a second arm defining a central region between the first arm and the second arm, and wherein the instrument lumen extends through the central region defined by the first arm and the second arm of the at least one ligation clip, wherein the first arm and the second arm of the at least one ligation clip are positioned between the inner wall and the outer wall of the cannula; and
at least one clip retention feature formed in the cannula body, wherein the at least one clip retention feature releasably holds the at least one ligation clip,
wherein the inner wall of the cannula separates the at least one ligation clip from the instrument lumen to maintain a fluid integrity of the instrument lumen.

2. The device of claim 1, wherein the first arm of the at least one ligation clip includes a first boss, wherein the second arm of the at least one ligation clip includes a second boss, and wherein the first boss and the second boss are each coupled to the at least one clip retention feature.

3. The device of claim 1, wherein the at least one ligation clip includes a plurality of ligation clips defining a clip stack, wherein the clip stack includes:
the plurality of ligation clips axially arranged about the instrument lumen, wherein the central region defined between the first arm and the second arm extends through the plurality of ligation clips, and wherein the instrument lumen extends through the central region of the plurality of ligation clips, and
wherein the at least one clip retention feature includes a plurality of clip retention features formed in the cannula body, and wherein each clip retention feature of the plurality of clip retention features releasably holds a respective ligation clip of the plurality of ligation clips.

4. The device of claim 3, wherein the first arm and the second arm of each ligation clip of the plurality of ligation clips are positioned between the inner wall and the outer wall of the cannula.

5. The device of claim 1, wherein the at least one ligation clip is graspable by an end effector of a robotic surgical system to separate the at least one ligation clip from the at least one clip retention feature.

6. An intra-cavity clip loading device, comprising:
a cannula including a cannula body defining an instrument lumen extending along a longitudinal axis of the cannula body, the cannula body including a slot;
a ligation clip supported in the cannula body and axially arranged about the instrument lumen; and
a clip retention feature formed in the cannula body and associated with the slot, the clip retention feature holding the ligation clip,
wherein the ligation clip is accessible by a clip applier through the slot formed in the cannula body.

7. The device of claim 6, wherein the slot is covered by a sheath positioned about the cannula body.

8. The device of claim 6, wherein the slot is located proximate a distal end portion of the cannula body.

9. The device of claim 6, further comprising:

a clip stack defined in the cannula body, the clip stack including:

a plurality of ligation clips in addition to the ligation clip, the plurality of ligation clips axially arranged about the instrument lumen; and a plurality of clip retention features in addition to the retention feature, the plurality of retention features formed in the cannula body, each clip retention feature of the plurality of clip retention features holding a ligation clip of the plurality of ligation clips, wherein, the cannula body includes a plurality of slots in addition to the slot, each slot of the plurality of slots is associated with a clip retention feature of the plurality of clip retention features, and each ligation clip of the plurality of ligation clips is accessible by a clip applier through a respective slot of the plurality of slots formed in the cannula body.

10. The device of claim 9, wherein each ligation clip of the plurality of ligation clips includes a first arm and a second arm defining a central region between the first arm and the second arm, and wherein the instrument lumen extends through the central region defined by the first arm and the second arm of each ligation clip of the plurality of ligation clips.

11. The device of claim 10, wherein the cannula includes an inner wall and an outer wall, the inner wall defining the instrument lumen, and wherein the first and second arms of each ligation clip of the plurality of ligation clips are positioned between the inner wall and the outer wall of the cannula.

12. The device of claim 11, wherein the inner wall of the cannula separates the plurality of ligation clips from the instrument lumen to maintain a fluid integrity of the instrument lumen.

13. The device of claim 6, wherein the ligation clip being accessible by a clip applier through the slot comprises the ligation clip being graspable by an end effector of a robotic surgical system.

14. An intra-cavity clip loading device, comprising:

a cannula including a cannula body defining an instrument lumen extending along a longitudinal axis of the cannula body, wherein the cannula includes a mate cap and an instrument seal formed in the mate cap to maintain a predetermined pressure in the instrument lumen;

at least one ligation clip axially arranged about the instrument lumen; and at least one clip retention feature formed in the cannula body, the at least one clip retention feature holding the at least one ligation clip.

15. The device of claim 14, wherein the at least one ligation clip includes a plurality of ligation clips, and the at least one clip retention feature includes a plurality of clip retention features, the device further comprising:

a clip stack defined in the cannula body, the clip stack including:

the plurality of ligation clips axially arranged about the instrument lumen; and the plurality of clip retention features formed in the cannula body, each clip retention feature of the plurality of clip retention features holding a ligation clip of the plurality of ligation clips.

16. The device of claim 15, wherein each ligation clip of the plurality of ligation clips includes a first arm and a second arm defining a central region between the first arm and the second arm, and wherein the instrument lumen extends through the central region defined by the first arm and the second arm of each ligation clip of the plurality of ligation clips.

17. The device of claim 16, wherein the cannula includes an inner wall and an outer wall, the inner wall defining the instrument lumen, and wherein the first and second arms of each ligation clip of the plurality of ligation clips are positioned between the inner wall and the outer wall of the cannula.

18. The device of claim 17, wherein the inner wall of the cannula separates the plurality of ligation clips from the instrument lumen to maintain a fluid integrity of the instrument lumen.

19. The device of claim 14 further including a distal seal configured to provide a barrier between an internal body cavity and the instrument lumen.

20. The device of claim 14, wherein the at least one ligation clip is graspable by an end effector of a robotic surgical system to separate the at least one ligation clip from the at least one clip retention feature.

* * * * *